United States Patent [19]
Borden et al.

[11] Patent Number: 5,712,148
[45] Date of Patent: Jan. 27, 1998

[54] DNA ENCODING A HUMAN BETAINE/GABA TRANSPORTER AND USES THEREOF

[75] Inventors: Laurence A. Borden, Hackensack; Kelli E. Smith, Wayne, both of N.J.; Richard L. Weinshank, New York, N.Y.

[73] Assignee: Synaptic Pharmaceutical Corporation, Paramus, N.J.

[21] Appl. No.: 543,881

[22] Filed: Oct. 17, 1995

Related U.S. Application Data

[63] Continuation of Ser. No. 334,858, Nov. 4, 1994, abandoned, which is a continuation of Ser. No. 1,738, Jan. 4, 1993, abandoned.

[51] Int. Cl.$^6$ .............................. C12N 5/00; C12N 1/14; C12N 15/00; C07H 21/04
[52] U.S. Cl. .............................. 435/240.2; 435/254.11; 435/320.1; 536/23.5
[58] Field of Search .............................. 435/240.2, 252.3, 435/254.11, 320.1; 530/350; 536/23.5, 24.31

[56] References Cited

U.S. PATENT DOCUMENTS 5,081,227  1/1992  Millan ............................ 530/328

OTHER PUBLICATIONS

Yamauchi, et al. (1992) J. Biol. Chem. 267:649–652.
Giros, et al. (1991) FEBS Letters 295:149–154.
Robey, et al. (1991) J. Biol. Chem. 266:10400–10405.
Pachelczyk, et al. (1991) Nature 350:350–354.
Blakely, et al. (1991) Anal. Biochem. 194:302–308.
Miller and Germain (1986) J. Exp. Med. 164:1478–1489.
Miller et al. (1986) J. Exp. Med. 164, 1478–1489.
Robey et al. (1991) J. Biol. Chem 266, 10400–10405.
ATCC Catalogue of Cell Lines and Hybridomas 6th Ed., pp. 2–3.
Borden et al. (1995) J. Neurochem. 64: 977–984.
Lopez–Corcuera, B., et al., Expression of a Mouse Brain cDNA Encoding Novel γ–Amino–butyric Acid Transporter, J. Biol. Chem. 1992, 267(25):17491–17493.

*Primary Examiner*—Robert A. Wax
*Assistant Examiner*—Lisa J. Hobbs
*Attorney, Agent, or Firm*—John P. White

[57] ABSTRACT

This invention provides an isolated nucleic acid molecule encoding a mammalian betaine/GABA transporter, an isolated nucleic acid molecule encoding a human betaine/GABA transporter, an isolated protein which is a mammalian betaine/GABA transporter, an isolated protein which is a human betaine/GABA transporter, vectors comprising an isolated nucleic acid molecule encoding a mammalian betaine/GABA transporter, vectors comprising an isolated nucleic acid molecule encoding a human betaine/GABA transporter, mammalian cells comprising such vectors, antibodies directed to the mammalian betaine/GABA transporter and antibodies directed to the human betaine/GABA transporter, nucleic acid probes useful for detecting nucleic acid molecules encoding mammalian betaine/GABA transporters and human betaine/GABA transporters, antisense oligonucleotides complementary to any sequences of a nucleic acid molecule which encodes a mammalian betaine/GABA transporter or a human betaine/GABA transporter, pharmaceutical compounds related to mammalian and human betaine/GABA transporters, and nonhuman transgenic animals which express DNA encoding a normal or a mutant mammalian or human betaine/GABA transporter. This invention further provides methods for determining substrate binding, detecting expression, drug screening, and treatments for alleviating abnormalities associated with mammalian betaine/GABA transporters and human betaine/GABA transporters.

14 Claims, 5 Drawing Sheets

FIG. 1A

```
     -200                -180                -160
      •                   •                   •
TTGGGACTCTCCTGGAGACCTGATGCCCACAGCCAAGCTGACCACAGGAGCCGGTGCTGG

-140                -120                -100
      •                   •                   •
GGACTGAGGGAAACTTAGAGTTCAGAGAGGGGGTGTGATTTGCCTGAGGTCACACAGCAA

-80                 -60                 -40
       •                   •                   •
GTTAGAGACCCAGCTCCACGACTCATTGTCTTGGCTTTGGCCCTCGTCATCCTGCCCACC

-20                  0                   20
       •                   •                   •
CAGCGGGGCTTCCCAACCCACCACACAGCCATGGACGGGAAGGTGGCAGTGCAAGAGTAT
                                 M  D  G  K  V  A  V  Q  E  Y 40                  60                  80
        •                   •                   •
GGGCCTCCTGCAGTCTCCTGGGTCCCCGAGGAGGGAGAGAAGTTGGACCAGGAAGACGAG
 G  P  P  A  V  S  W  V  P  E  E  G  E  K  L  D  Q  E  D  E 100                 120                 140
       •                   •                   •
GACCAGGTGAAGGATCGGGGCCAATGGACCAACAAGATGGAGTTTGTGCTGTCAGTGGCC
 D  Q  V  K  D  R  G  Q  W  T  N  K  M  E  F  V  L  S  V  A 160                 180                 200
       •                   •                   •
GGGGAGATCATTGGGCTGGGCAATGTCTGGAGGTTTCCCTATCTCTGCTACAAAAACGGA
 G  E  I  I  G  L  G  N  V  W  R  F  P  Y  L  C  Y  K  N  G 220                 240                 260
       •                   •                   •
GGTGGAGCCTTCTTCATCCCCTACTTCATCTTCTTCTTTGTCTGCGGCATCCCGGTGTTC
 G  G  A  F  F  I  P  Y  F  I  F  F  F  V  C  G  I  P  V  F 280                 300                 320
       •                   •                   •
TTCCTGGAGGTGGCGTTGGGCCAATACACCAGCCAAGGGAGTGTCACAGCCTGGAGGAAG
 F  L  E  V  A  L  G  Q  Y  T  S  Q  G  S  V  T  A  W  R  K 340                 360                 380
       •                   •                   •
ATCTGCCCCCTCTTCCAGGGCATTGGTCTGGCATCTGTGGTCATCGAGTCATATTTGAAT
 I  C  P  L  F  Q  G  I  G  L  A  S  V  V  I  E  S  Y  L  N
```

FIG. 1B

```
                400                      420                      440
          GTCTACTACATCATCATCCTTGCCTGGGCTCTCTTCTACCTGTTCAGCTCCTTCACCTCT
           V  Y  Y  I  I  I  L  A  W  A  L  F  Y  L  F  S  S  F  T  S 460                      480                      500
          GAGCTGCCCTGGACGACCTGCAACAACTTTTGGAACACAGAGCATTGCACGGACTTTCTG
           E  L  P  W  T  T  C  N  N  F  W  N  T  E  H  C  T  D  F  L 520                      540                      560
          AACCACTCAGGAGCCGGCACAGTGACCCCATTTGAGAATTTTACCTCACCTGTCATGGAA
           N  H  S  G  A  G  T  V  T  P  F  E  N  F  T  S  P  V  M  E 580                      600                      620
          TTCTGGGAGAGACGAGTTCTGGGCATCACCTCGGGCATCCATGACCTGGGCTCCCTGCGC
           F  W  E  R  R  V  L  G  I  T  S  G  I  H  D  L  G  S  L  R 640                      660                      680
          TGGGAGCTGGCCCTGTGCCTCCTGCTCGCCTGGGTCATCTGCTATTTCTGCATCTGGAAG
           W  E  L  A  L  C  L  L  L  A  W  V  I  C  Y  F  C  I  W  K 700                      720                      740
          GGGGTCAAGTCCACAGGCAAGGTGGTTTATTTCACAGCCACGTTTCCGTACCTGATGCTT
           G  V  K  S  T  G  K  V  V  Y  F  T  A  T  F  P  Y  L  M  L 760                      780                      800
          GTCATTTTGCTGATCAGAGGTGTCACCCTTCCCGGAGCCTACCAGGGCATCATCTACTAC
           V  I  L  L  I  R  G  V  T  L  P  G  A  Y  Q  G  I  I  Y  Y 820                      840                      860
          TTGAAGCCAGATTTGTTCCGCCTCAAGGACCCTCAGGTGTGGATGGATGCGGGCACCCAG
           L  K  P  D  L  F  R  L  K  D  P  Q  V  W  M  D  A  G  T  Q 880                      900                      920
          ATCTTCTTCTCCTTTGCCATCTGCCAGGGGTGCCTGACAGCCCTGGGCAGCTACAACAAG
           I  F  F  S  F  A  I  C  Q  G  C  L  T  A  L  G  S  Y  N  K 940                      960                      980
          TATCACAACAACTGCTACAAGGACTGCATCGCCCTCTGCTTCCTGAACAGTGCCACCAGC
           Y  H  N  N  C  Y  K  D  C  I  A  L  C  F  L  N  S  A  T  S
```

FIG. 1C

```
         1000                1020                1040
          .                   .                   .
TTTGTGGCTGGGTTTGTTGTCTTCTCCATCCTGGGCTTCATGTCCCAAGAGCAAGGGGTG
 F  V  A  G  F  V  V  F  S  I  L  G  F  M  S  Q  E  Q  G  V 1060                1080                1100
          .                   .                   .
CCCATTTCTGAAGTGGCCGAGTCAGGTCCTGGGCTGGCCTTCATCGCCTTCCCCAAGGCT
 P  I  S  E  V  A  E  S  G  P  G  L  A  F  I  A  F  P  K  A 1120                1140                1160
          .                   .                   .
GTGACTATGATGCCCTTATCCCAGCTGTGGTCCTGCCTGTTCTTTATCATGCTCATATTC
 V  T  M  M  P  L  S  Q  L  W  S  C  L  F  F  I  M  L  I  F 1180                1200                1220
          .                   .                   .
CTAGGGCTGGACAGCCAGTTTGTCTGTGTGGAGTGCCTGGTGACAGCCTCCATAGACATG
 L  G  L  D  S  Q  F  V  C  V  E  C  L  V  T  A  S  I  D  M 1240                1260                1280
          .                   .                   .
TTCCCCAGGCAGCTCCGGAAGAGCGGGCGGCGCGAGCTCCTCATCCTCACCATCGCCGTC
 F  P  R  Q  L  R  K  S  G  R  R  E  L  L  I  L  T  I  A  V 1300                1320                1340
          .                   .                   .
ATGTGCTACCTGATAGGGCTTTTCCTGGTCACCGAGGGCGGGATGTACATCTTCCAGCTG
 M  C  Y  L  I  G  L  F  L  V  T  E  G  G  M  Y  I  F  Q  L 1360                1380                1400
          .                   .                   .
TTTGACTACTATGCTTCCAGTGGCATATGCCTGCTGTTCCTGTCATTGTTTGAAGTGGTC
 F  D  Y  Y  A  S  S  G  I  C  L  L  F  L  S  L  F  E  V  V 1420                1440                1460
          .                   .                   .
TGCATAAGCTGGGTGTATGGGGCGGACCGTTTCTATGACAACATTGAGGACATGATTGGC
 C  I  S  W  V  Y  G  A  D  R  F  Y  D  N  I  E  D  M  I  G 1480                1500                1520
          .                   .                   .
TACCGGCCATGGCCCCTGGTGAAGATCTCCTGGCTCTTCCTGACCCCTGGACTTTGCCTG
 Y  R  P  W  P  L  V  K  I  S  W  L  F  L  T  P  G  L  C  L 1540                1560                1580
          .                   .                   .
GCCACTTTCCTCTTCTCCTTGAGCAAGTACACCCCCCTCAAGTACAACAACGTCTATGTG
 A  T  F  L  F  S  L  S  K  Y  T  P  L  K  Y  N  N  V  Y  V
```

FIG. 1D

```
         1600                  1620                  1640
          .                     .                     .
TACCCGCCCTGGGGATACTCCATTGGCTGGTTCCTGGCTCTGTCCTCCATGGTCTGTGTC
 Y  P  P  W  G  Y  S  I  G  W  F  L  A  L  S  S  M  V  C  V 1660                  1680                  1700
          .                     .                     .
CCACTCTTCGTCGTCATCACCCTCCTGAAGACTCGGGGTCCTTTCAGGAAGCGTCTGCGT
 P  L  F  V  V  I  T  L  L  K  T  R  G  P  F  R  K  R  L  R 1720                  1740                  1760
          .                     .                     .
CAGCTCATCACCCCTGACTCCAGTCTGCCACAGCCCAAGCAACATCCCTGCTTGGATGGC
 Q  L  I  T  P  D  S  S  L  P  Q  P  K  Q  H  P  C  L  D  G 1780                  1800                  1820
          .                     .                     .
AGTGCTGGCCGGAACTTTGGGCCCTCCCCAACAAGGGAAGGACTGATAGCCGGGGAGAAG
 S  A  G  R  N  F  G  P  S  P  T  R  E  G  L  I  A  G  E  K 1840                  1860                  1880
          .                     .                     .
GAGACCCATTTGTAGGGTGTGACCAGAGGCCAGGCGGCTCCTAAGCCGGGAACCTAGGTC
 E  T  H  L 1900                  1920                  1940
          .                     .                     .
AGGGCCACCCTCCATTCTCAGCGGACAGCCTCTGCCTCTGTCTCCTGCCACAATCCTGCT 1960                  1980                  2000
          .                     .                     .
GGGAACCTCTGGAGAGCCACAGGCACCCCAGCTGGAGGCCAGACTCCTCTCTTGTG
```

DNA ENCODING A HUMAN BETAINE/GABA TRANSPORTER AND USES THEREOF

This application is a continuation of U.S. Ser. No. 08/334,858, filed Nov. 4, 1994, now abandoned, which is a continuation of U.S. Ser. No. 08/001,738, filed Jan. 4, 1993, now abandoned.

BACKGROUND OF THE INVENTION

Throughout this application various publications are referred to by partial citations within parenthesis. Full citations for these publications may be found at the end of the specification immediately preceding the claims. The disclosures of these publications, in their entireties, are hereby incorporated by reference into this application in order to more fully describe the state of the art to which this invention pertains.

Cell surface transporters are critical to the survival and proper functioning of cells. Transporters serve in virtually all cells as the conduit by which essential nutrients such as glucose and amino acids gain access to the cell interior (for review see Silverman, 1991; Christensen, 1984). Transporters also play a critical role in the ability of cells to adapt to alterations in osmolarity. Within the nervous system transporters additionally serve a more specialized function. Specifically, high-affinity transporters are responsible for removing neurotransmitters from the synaptic cleft, thereby terminating neurotransmission (for review, see Kanner and Schuldiner, 1987).

The application of molecular biological techniques to the study of neurotransmitter transporters has greatly advanced our understanding of this class of proteins. Clones have now been obtained for many of the major neurotransmitters including γ-aminobutyric acid (GABA) neurotransmitters including γ-aminobutyric acid (GABA) (Guastella et al., 1990; Nelson et al., 1990; Borden et al., 1992; Liu et al., 1992a), glycine (Smith et al., 1992a; Guastella et al., 1992; Liu et al., 1992b), norepinephrine (Pacholczyk et al., 1991), dopamine (Shimada et al., 1991; Usdin et al., 1991; Giros et al., 1992), and serotonin (Hoffman et al., 1991; Blakely et al., 1991).

Transporters have also been obtained for molecules with presumed neuromodulatory roles, such as taurine (Smith et al., 1992b; Uchida et al., 1992) and proline (Fremeau, Jr. et al., 1992). These transporters have in common a requirement for sodium and chloride, and they show considerable structural similarity including 12 putative transmembrane domains. More recently clones have been obtained that encode glutamate transporters (Storck et al., 1992; Pines et al., 1992; Kanai and Hediger, 1992). These transporters are structurally unrelated to the others, perhaps consistent with their different ionic requirements (for review, see Amara, 1992).

Cloning of GABA transporters has revealed considerable diversity of this system. In addition to the original GABA transporter clone obtained from rat brain (GAT-1; Guastella et al., 1990), we have identified two additional rat brain clones encoding high-affinity GABA transporters which we term GAT-2 and GAT-3 (Borden et al., 1992). An additional and unanticipated member of this class is a betaine transporter, cloned from MDCK dog kidney cells by Handler and coworkers (Yamauchi et al., 1992). Betaine is an important osmolyte in the kidney, and possibly other organs. Interestingly, this transporter was found to have higher affinity for GABA than for betaine, suggesting a role in GABAergic transmission. However, transporter mRNA was not detected in dog brain (Yamauchi et al., 1992). Subsequently, Lopez-Corcuera et al. (1992) isolated from mouse brain a cDNA clone which displays both sequence and pharmacological similarity to the dog kidney clone. We now report the cloning and expression of a related clone from a human brain cDNA library. Although the function of this transporter in the nervous system is not understood, it may serve to regulate both GABAergic transmission and osmolarity.

SUMMARY OF THE INVENTION

This invention provides an isolated nucleic acid molecule encoding a mammalian betaine/GABA transporter. In one embodiment of this invention the isolated nucleic acid molecule encodes a human betaine/GABA transporter. In another embodiment of this invention, the nucleic acid molecule encoding the human betaine/GABA transporter comprises a plasmid designated pcEXV-hBGT (ATCC Accession No. 75393, deposited Dec. 30, 1992).

This invention provides a nucleic acid probe comprising a nucleic acid molecule of at least 15 nucleotides capable of specifically hybridizing with a sequence included within the sequence of a nucleic acid molecule encoding a mammalian betaine/GABA transporter. This invention also provides a nucleic acid probe comprising a nucleic acid molecule of at least 15 nucleotides capable of specifically hybridizing with a sequence included within the sequence of a nucleic acid molecule encoding a human betaine/GABA transporter.

This invention further provides an antisense oligonucleotide having a sequence capable of binding specifically to an mRNA molecule encoding a mammalian betaine/GABA transporter so as to prevent translation of the mRNA molecule. This invention also provides an antisense oligonucleotide having a sequence capable of binding specifically to an mRNA molecule encoding a human betaine/GABA transporter so as to prevent translation of the mRNA molecule.

This invention provides a monoclonal antibody directed to a mammalian betaine/GABA transporter. This invention further provides a monoclonal antibody directed to a human betaine/GABA transporter.

This invention provides a pharmaceutical composition comprising an amount of a substance effective to alleviate the abnormalities resulting from overexpression of a mammalian betaine/GABA transporter and a pharmaceutically acceptable carrier as well as a pharmaceutical composition comprising an amount of a substance effective to alleviate abnormalities resulting from underexpression of betaine/GABA transporter and a pharmaceutically acceptable carrier.

A pharmaceutical composition comprising an amount of a substance effective to alleviate the abnormalities resulting from overexpression of a human betaine/GABA transporter and a pharmaceutically acceptable carrier as well as a pharmaceutical composition comprising an amount of a substance effective to alleviate abnormalities resulting from underexpression of a human betaine/GABA transporter and a pharmaceutically acceptable carrier is also provided by this invention.

This invention also provides a transgenic, nonhuman mammal whose genome comprises DNA encoding a mammalian betaine/GABA transporter so positioned within such genome as to be transcribed into antisense mRNA complementary to mRNA encoding the betaine/GABA transporter and when hybridized to mRNA encoding the betaine/GABA transporter, the complementary mRNA reduces the translation of the mRNA encoding the betaine/GABA transporter.

This invention also provides a transgenic, nonhuman mammal whose genome comprises DNA encoding a human betaine/GABA transporter so positioned within such genome as to be transcribed into antisense mRNA which is complementary to mRNA encoding the human betaine/GABA transporter and when hybridized to mRNA encoding the human betaine/GABA transporter, the antisense mRNA thereby reduces the translation of mRNA encoding the human betaine/GABA transporter.

This invention also provides a transgenic, nonhuman mammal whose genome comprises DNA encoding a mammalian betaine/GABA transporter so positioned within such genome as to be transcribed into antisense mRNA which is complementary to mRNA encoding the transporter and when hybridized to mRNA encoding the transporter, the antisense mRNA thereby prevents the translation of mRNA encoding the transporter.

This invention also provides a transgenic, nonhuman mammal whose genome comprises DNA encoding a human betaine/GABA transporter so positioned within such genome as to be transcribed into antisense mRNA which is complementary to mRNA encoding the betaine/GABA transporter and when hybridized to mRNA encoding the betaine/GABA transporter, the antisense mRNA thereby prevents the translation of mRNA encoding the human betaine/GABA transporter.

This invention provides a method of screening drugs to identify drugs which specifically interact with, and bind to, a mammalian betaine/GABA transporter on the surface of a cell which comprises contacting a mammalian cell comprising an isolated DNA molecule encoding a mammalian betaine/GABA transporter, the protein encoded thereby is expressed on the cell surface, with a plurality of drugs, determining those drugs which bind to the mammalian cell, and thereby identifying drugs which specifically interact with, and bind to, a mammalian betaine/GABA transporter.

This invention provides a method of screening drugs to identify drugs which specifically interact with, and bind to, a human betaine/GABA transporter on the surface of a cell which comprises contacting a mammalian cell comprising an isolated DNA molecule encoding a human betaine/GABA transporter, the protein encoded thereby is expressed on the cell surface, with a plurality of drugs, determining those drugs which bind to the mammalian cell, and thereby identifying drugs which specifically interact with, and bind to, a human betaine/GABA transporter.

This invention also provides a method of determining the physiological effects of expressing varying levels of a mammalian betaine/GABA transporter which comprises producing a transgenic nonhuman animal whose levels of mammalian betaine/GABA transporter expression are varied by use of an inducible promoter which regulates mammalian betaine/GABA transporter expression.

This invention also provides a method of determining the physiological effects of expressing varying levels of a human betaine/GABA transporter which comprises producing a transgenic nonhuman animal whose levels of human betaine/GABA transporter expression are varied by use of an inducible promoter which regulates human betaine/GABA transporter expression.

This invention further provides a method of determining the physiological effects of expressing varying levels of a mammalian betaine/GABA transporter which comprises producing a panel of transgenic nonhuman animals each expressing a different amount of mammalian betaine/GABA transporter.

This invention further provides a method of determining the physiological effects of expressing varying levels of a human betaine/GABA transporter which comprises producing a panel of transgenic nonhuman animals each expressing a different amount of human betaine/GABA transporter.

This invention provides a method for diagnosing a predisposition to a disorder associated with the expression of a specific mammalian betaine/GABA transporter allele which comprises: a.) obtaining DNA of subjects suffering from the disorder; b.) performing a restriction digest of the DNA with a panel of restriction enzymes; c.) electrophoretically separating the resulting DNA fragments on a sizing gel; d.) contacting the resulting gel with a nucleic acid probe capable of specifically hybridizing to DNA encoding a mammalian betaine/GABA transporter and labelled with a detectable marker; e.) detecting labelled bands which have hybridized to the DNA encoding a mammalian betaine/GABA transporter labelled with a detectable marker to create a unique band pattern specific to the DNA of subjects suffering from the disorder; f.) preparing DNA obtained for diagnosis by steps a–e; and g.) comparing the unique band pattern specific to the DNA of subjects suffering from the disorder from step e and the DNA obtained for diagnosis from step f to determine whether the patterns are the same or different and to diagnose thereby predisposition to the disorder if the patterns are the same.

This invention provides a method for diagnosing a predisposition to a disorder associated with the expression of a specific human betaine/GABA transporter allele which comprises: a.) obtaining DNA of subjects suffering from the disorder; b.) performing a restriction digest of the DNA with a panel of restriction enzymes; c.) electrophoretically separating the resulting DNA fragments on a sizing gel; d.) contacting the resulting gel with a nucleic acid probe capable of specifically hybridizing to DNA encoding a human betaine/GABA transporter and labelled with a detectable marker; e.) detecting labelled bands which have hybridized to the DNA encoding a human betaine/GABA transporter labelled with a detectable marker to create a unique band pattern specific to the DNA of subjects suffering from the disorder; f.) preparing DNA obtained for diagnosis by steps a–e; and g.) comparing the unique band pattern specific to the DNA of subjects suffering from the disorder from step e and the DNA obtained for diagnosis from step f to determine whether the patterns are the same or different and to diagnose thereby predisposition to the disorder if the patterns are the same.

This invention provides a method for determining whether a substrate not known to be capable of binding to a mammalian betaine/GABA transporter can bind to the mammalian betaine/GABA transporter which comprises contacting a mammalian cell comprising an isolated DNA molecule encoding the betaine/GABA transporter with the substrate under conditions permitting binding of substrates known to bind to a transporter, detecting the presence of any of the substrate bound to the betaine/GABA transporter, and thereby determining whether the substrate binds to the betaine/GABA transporter.

This invention provides a method for determining whether a substrate not known to be capable of binding to a human betaine/GABA transporter can bind to a human betaine/GABA transporter which comprises contacting a mammalian cell comprising an isolated DNA molecule encoding the human betaine/GABA transporter with the substrate under conditions permitting binding of substrates known to bind to a transporter, detecting the presence of any of the substrate bound to the human betaine/GABA transporter, and thereby determining whether the substrate binds to the human betaine/GABA transporter.

BRIEF DESCRIPTION OF THE FIGURES

FIGS. 1a–1d. Nucleotide Sequence and Deduced Amino Acid Sequence of the Human Betaine/GABA Transporter. Nucleotides are presented in the 5' to 3' orientation and the coding region is numbered starting from the putative initiating methionine. DNA sequence was determined by the chain termination method of Sanger (1977) on denatured double-stranded plasmid templates using Sequenase. Deduced amino acid sequence (single letter abbreviation) by translation of a long open reading frame is shown.

DETAILED DESCRIPTION OF THE INVENTION

Figure 2:
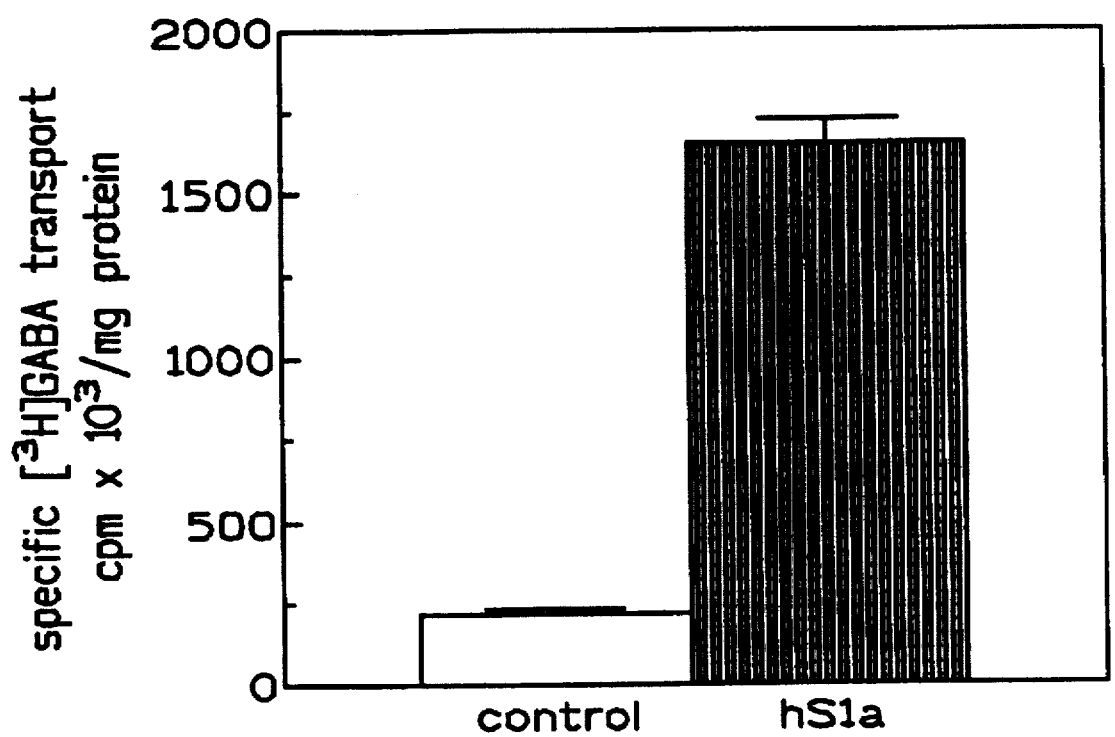
FIG. 2. GABA transport by COS cells transfected with hS1a. Substrate-attached non-transfected COS cells (control) or COS cells transiently transfected with hS1a were incubated for 10 minutes (37° C.) with 50 nM [$^3$H] GABA in HBS, washed, and radioactivity determined. Data show specific uptake, expressed as cpm per mg cellular protein. Data (mean±SEM) are from a single experiment that was repeated many times with similar results.

This invention provides an isolated nucleic acid molecule encoding a mammalian betaine/GABA transporter. As used herein, the term "isolated nucleic acid molecule" means a non-naturally occurring nucleic acid molecule that is, a molecule in a form which does not occur in nature. Examples of such an isolated nucleic acid molecule are an RNA, cDNA, or isolated genomic DNA molecule encoding a mammalian betaine/GABA transporter. As used herein, "betaine/GABA transporter" means a molecule which, under physiologic conditions, is substantially specific for the neurotransmitter GABA and betaine, is saturable and of high affinity for GABA and betaine. One embodiment of this invention is an isolated human nucleic acid molecule encoding a mammalian betaine/GABA transporter. Another preferred embodiment of this invention is an isolated nucleic acid molecule encoding a human betaine/GABA transporter. Such molecules may have coding sequences substantially the same as the coding sequences shown in FIGS. 1A–1D (SEQ ID NO. 1). The DNA molecule of FIG. 1 (Sequence I.D. No. 1) encodes the sequence of a human betaine/GABA transporter gene. One means of isolating a mammalian betaine/GABA transporter is to probe a mammalian genomic library with a natural or artificially designed DNA probe, using methods well known in the art. In the preferred embodiment of this invention, the mammalian betaine/GABA transporter is a human protein and the nucleic acid molecules encoding them are isolated from a human cDNA library or a human genomic DNA library. Degenerate oligonucleotide primers the sequences of which are derived from comparisons between conserved regions of several transporters are useful for identifying a nucleic acid molecule encoding a mammalian betaine/GABA transporter, obtaining a probe to a mammalian betaine/GABA transporter and for isolating a nucleic acid molecule encoding a mammalian betaine/GABA transporter. DNA and cDNA molecules which encode a human or mammalian betaine/GABA transporter are used to obtain complementary genomic DNA, cDNA or RNA from human, mammalian or other animal sources, or to isolate related cDNA or genomic clones by the screening of cDNA or genomic DNA libraries, by methods described in more detail below. Transcriptional regulatory elements from the 5' untranslated region of the isolated clone, and other stability, processing, transcription, translation, and tissue specificity determining regions from the 3' and 5' untranslated regions of the isolated gene are thereby obtained.

A sequence derived from the DNA encoding a human or a mammalian betaine/GABA transporter such as that derived from the sequence encoding the human betaine/GABA transporter in FIGS. 1A–1D (SEQ ID NO. 1) can be used to identify and isolate human or a mammalian RNA or DNA encoding a betaine/GABA transporter subtype or a related transporter. Transporter subtypes may be products of the same gene or more than one gene. Products of the same gene are generated by alternative splicing of the RNA encoding the transporter, by rearrangements of the same gene encoding the transporter or by other means.

This invention provides an isolated nucleic acid molecule which has been so mutated as to be incapable of encoding a molecule having normal transporter activity, and not expressing native transporter. An example of a mutated nucleic acid molecule provided by this invention is an isolated nucleic acid molecule which has an in-frame stop codon inserted into the coding sequence such that the transcribed RNA is not translated into a protein having normal transporter activity.

This invention provides a cDNA molecule encoding a mammalian betaine/GABA transporter. This invention further provides a cDNA molecule encoding a human betaine/GABA transporter. The cDNA encoding the mammalian or human betaine\GABA transporter has coding sequence substantially the same as the coding sequence shown in FIGS. 1A–1D (Sequence I.D. No. 1). These molecules and their equivalents are obtained by the means described above.

This invention also provides an isolated protein which is a mammalian GABA transporter. In a preferred embodiment of this invention, the protein is a human GABA transporter protein having an amino acid sequence substantially the same as the sequence shown in FIGS. 1A–1D (Sequence I.D. Nos. 1 and 2). As used herein, the term "isolated protein" is intended to encompass a protein molecule free of other cellular components. One means for obtaining an isolated betaine/GABA transporter is to express DNA encoding the transporter in a suitable host, such as a bacterial, yeast, or mammalian cell, using methods well known to those skilled in the art, and recovering the transporter protein after it has been expressed in such a host, again using methods well known in the art. The transporter may also be isolated from cells which express it, in particular from cells which have been transfected with the expression vectors described below in more detail.

This invention also provides a vector comprising an isolated nucleic acid molecule such as DNA, RNA, or cDNA, encoding a mammalian betaine/GABA transporter. This invention also provides a vector comprising an isolated nucleic acid molecule such as DNA, RNA, or cDNA, encoding a human betaine/GABA transporter.

Examples of vectors are viruses such as bacteriophages (such as phage lambda), cosmids, plasmids (such as pUC18, available from Pharmacia, Piscataway, N.J.), and other recombination vectors. Nucleic acid molecules are inserted into vector genomes by methods well known to those skilled in the art. Examples of such plasmids are plasmids comprising cDNA having a coding sequence substantially the same as the coding sequence shown in FIGS. 1A–1D (Seq. I.D. No. 1) and designated pcEXV-hBGT (ATCC Accession NO. 75393, deposited Dec. 30, 1992). Alternatively, to obtain these vectors, insert and vector DNA can both be exposed to a restriction enzyme to create complementary ends on both molecules which base pair with each other and are then ligated together with a ligase. Alternatively, linkers can be ligated to the insert DNA which correspond to a restriction site in the vector DNA, which is then digested with the restriction enzyme which cuts at that site. Other means are also available.

This invention also provides vectors comprising a DNA molecule encoding a mammalian betaine/GABA transporter adapted for expression in a bacterial cell, a yeast cell, or a mammalian cell which additionally comprise the regulatory elements necessary for expression of the DNA in the bacterial, yeast, or mammalian cells so located relative to the DNA encoding a mammalian betaine/GABA transporter or to the DNA encoding a human betaine/GABA transporter as to permit expression thereof. DNA having coding sequences substantially the same as the coding sequence shown in FIGS. 1A–1D may usefully be inserted into the vectors to express mammalian or human betaine/GABA transporters. Regulatory elements required for expression include promoter sequences to bind RNA polymerase and transcription initiation sequences for ribosome binding. For example, a bacterial expression vector includes a promoter such as the lac promoter and for transcription initiation the Shine-Dalgarno sequence and the start codon AUG (Maniatis, et al., Molecular Cloning, Cold Spring Harbor Laboratory, 1982). Similarly, a eukaryotic expression vector includes a heterologous or homologous promoter for RNA polymerase II, a downstream polyadenylation signal, the start codon AUG, and a termination codon for detachment of the ribosome. Such vectors may be obtained commercially or assembled from the sequences described by methods well known in the art, for example the methods described above for constructing vectors in general. Expression vectors are useful to produce cells that express the transporter. Certain uses for such cells are described in more detail below.

In one embodiment of this invention a plasmid is adapted for expression in a bacterial, yeast, or, in particular, a mammalian cell wherein the plasmid comprises a DNA molecule encoding a mammalian betaine/GABA transporter and the regulatory elements necessary for expression of the DNA in the bacterial, yeast, or mammalian cell so located relative to the DNA encoding a mammalian betaine/GABA transporter as to permit expression thereof. In another embodiment of this invention a plasmid is adapted for expression in a bacterial, yeast, or, in particular, a mammalian cell wherein the plasmid comprises a DNA molecule encoding a human betaine/GABA transporter and the regulatory elements necessary for expression of the DNA in the bacterial, yeast, or mammalian cell so located relative to the DNA encoding a human betaine/GABA transporter to permit expression thereof. Suitable plasmids may include, but are not limited to plasmids adapted for expression in a mammalian cell, e.g., EVJB or EXV. Examples of such plasmids adapted for expression in a mammalian cell are plasmids comprising cDNA having coding sequences substantially the same as the coding sequence shown in FIGS. 1A–1D (SEQ ID NO. 1) and the regulatory elements necessary for expression of the DNA in the mammalian cell. A plasmid adapted for expression in a mammalian cell comprising the DNA encoding a human betaine/GABA transporter has been designated pcEXV-hBGT and deposited under ATCC Accession No. 75393, deposited Dec. 30, 1992. Those skilled in the art will readily appreciate that numerous plasmids adapted for expression in a mammalian cell which comprise DNA encoding a mammalian or human betaine/GABA transporter and the regulatory elements necessary to express such DNA in the mammalian cell may be constructed utilizing existing plasmids and adapted as appropriate to contain the regulatory elements necessary to express the DNA in the mammalian cell. The plasmids may be constructed by the methods described above for expression vectors and vectors in general, and by other methods well known in the art.

The deposits discussed supra were made pursuant to, and in satisfaction of, the provisions of the Budapest Treaty on the International Recognition of the Deposit of Microorganisms for the Purpose of Patent Procedure with the American Type Culture Collection (ATCC), 12301 Parklawn Drive, Rockville, Md. 20852.

This invention provides a mammalian cell comprising a DNA molecule encoding a mammalian betaine/GABA transporter, such as a mammalian cell comprising a plasmid adapted for expression in a mammalian cell, which comprises a DNA molecule encoding a mammalian betaine/GABA transporter and the regulatory elements necessary for expression of the DNA in the mammalian cell so located relative to the DNA encoding a mammalian transporter as to permit expression thereof. This invention also provides a mammalian cell comprising a DNA molecule encoding a human betaine/GABA transporter, such as a mammalian cell comprising a plasmid adapted for expression in a mammalian cell, which comprises a DNA molecule encoding a human betaine/GABA transporter and the regulatory elements necessary for expression of the DNA in the mammalian cell so located relative to the DNA encoding a human transporter as to permit expression thereof. Numerous mammalian cells may be used as hosts, including, but not limited to, the mouse fibroblast cell NIH3T3, CHO cells, HeLa cells, Ltk⁻ cells, Cos cells, etc. Expression plasmids such as that described supra may be used to transfect mammalian cells by methods well known in the art such as calcium phosphate precipitation, or DNA encoding these transporters may be otherwise introduced into mammalian cells, e.g., by microinjection, to obtain mammalian cells which comprise DNA, e.g., cDNA or a plasmid, encoding a mammalian or a human betaine/GABA transporter. Cell line L-BGT was deposited with the ATCC on Dec. 30, 1992, and was accorded ATCC Accession No. CRL-11229.

This invention provides a nucleic acid probe comprising a nucleic acid molecule of at least 15 nucleotides capable of specifically hybridizing with a sequence included within the sequence of a nucleic acid molecule encoding a mammalian betaine/GABA transporter. This invention also provides a nucleic acid probe comprising a nucleic acid molecule of at least 15 nucleotides capable of specifically hybridizing with a sequence included within the sequence of a nucleic acid molecule encoding a human betaine/GABA transporter, for example with a coding sequence included within the sequence shown in FIGS. 1A–1D (SEQ ID NO. 1). As used herein, the phrase "Specifically hybridizing" means the ability of a nucleic acid molecule to recognize a nucleic acid sequence complementary to its own and to form double-helical segments through hydrogen bonding between complementary base pairs. Nucleic acid probe technology is well known to those skilled in the art who will readily appreciate that such probes may vary greatly in length and may be labeled with a detectable label, such as a radioisotope or fluorescent dye, to facilitate detection of the probe. Detection of nucleic acid encoding a mammalian betaine/GABA transporter or human betaine/GABA transporter is useful as a diagnostic test for any disease process in which levels of expression of the corresponding betaine/GABA are altered. DNA probe molecules are produced by insertion of a DNA molecule which encodes the mammalian or human betaine/GABA transporter or fragments thereof into suitable vectors, such as plasmids or bacteriophages, followed by insertion into suitable bacterial host cells and replication and harvesting of the DNA probes, all using methods well known in the art. For example, the DNA may be extracted from a cell lysate using phenol and ethanol, digested with restriction enzymes corresponding to the insertion sites of the DNA into the vector (discussed above), electrophoresed, and cut out of the resulting gel. Examples of such DNA molecules are shown in FIGS. 1A–1D (SEQ ID NO. 1). The probes are useful for 'in situ' hybridization or in order to locate tissues which express this gene family, or for other hybridization assays for the presence of these genes or their mRNA in various biological tissues. In addition, synthesized oligonucleotides (produced by a DNA synthesizer) complementary to the sequence of a DNA molecule which encodes a mammalian betaine/GABA transporter or complementary to the sequence of a DNA molecule which encodes a human betaine/GABA transporter, are useful as probes for these genes, for their associated mRNA, or for the isolation of related genes by homology screening of genomic or cDNA libraries, or by the use of amplification techniques such as the Polymerase Chain Reaction.

This invention also provides a method of detecting expression of a mammalian betaine/GABA transporter on the surface of a cell by detecting the presence of mRNA coding for the mammalian betaine/GABA transporter. This invention further provides a method of detecting the expression of a human betaine/GABA transporter on the surface of the cell by detecting the presence of mRNA coding for the corresponding betaine/GABA transporter. These methods comprise obtaining total mRNA from the cell using methods well known in the art and contacting the mRNA so obtained with a nucleic acid probe as described hereinabove, under hybridizing conditions, detecting the presence of mRNA hybridized to the probe, and thereby detecting the expression of the transporter by the cell. Hybridization of probes to target nucleic acid molecules such as mRNA molecules employs techniques well known in the art. However, in one embodiment of this invention, nucleic acids are extracted by precipitation from lysed cells and the mRNA is isolated from the extract using a column which binds the poly-A tails of the mRNA molecules (Maniatis et al. 1982). The mRNA is then exposed to radioactively labelled probe on a nitrocellulose membrane, and the probe hybridizes to and thereby labels complementary mRNA sequences. Binding may be detected by autoradiography or scintillation counting. However, other methods for performing these steps are well known to those skilled in the art, and the discussion above is merely an example.

This invention provides an antisense oligonucleotide having a sequence capable of binding specifically with any sequences of an mRNA molecule which encodes a mammalian betaine GABA transporter so as to prevent translation of the mammalian betaine/GABA transporter. This invention provides an antisense oligonucleotide having a sequence capable of binding specifically with any sequences of an mRNA molecule which encodes a human betaine/GABA transporter so as to prevent translation of the human betaine/GABA transporter. As used herein, the phrase "binding specifically" means the ability of an antisense oligonucleotide to recognize a nucleic acid sequence complementary to its own and to form double-helical segments through hydrogen bonding between complementary base pairs. The antisense oligonucleotide may have a sequence capable of binding specifically with any sequences of the cDNA molecules whose sequences are shown in FIGS. 1A–1D (SEQ ID NO. 1). A particular example of an antisense oligonucleotide is an antisense oligonucleotide comprising chemical analogues of nucleotides.

This invention also provides a pharmaceutical composition comprising an effective amount of the oligonucleotide described above effective to reduce expression of a mammalian betaine/GABA transporter by passing through a cell membrane and binding specifically with mRNA encoding a mammalian betaine/GABA transporter in the cell so as to prevent its translation and a pharmaceutically acceptable hydrophobic carrier capable of passing through a cell membrane. This invention also provides a pharmaceutical composition comprising an effective amount of the oligonucleotide described above effective to reduce expression of a human betaine/GABA transporter by passing through a cell membrane and binding specifically with mRNA encoding a human betaine/GABA transporter in the cell so as to prevent its translation and a pharmaceutically acceptable hydrophobic carrier capable of passing through a cell membrane. As used herein, the term "pharmaceutically acceptable carrier" encompasses any of the standard pharmaceutical carriers, such as a phosphate buffered saline solution, water, and emulsions, such as an oil/water or water/oil emulsion, and various types of wetting agents. The oligonucleotide may be coupled to a substance which inactivates mRNA, such as a ribozyme. The pharmaceutically acceptable hydrophobic carrier capable of passing through cell membranes may also comprise a structure which binds to a transporter specific for a selected cell type and is thereby taken up by cells of the selected cell type. The structure may be part of a protein known to bind a cell-type specific transporter, for example an insulin molecule, which would target pancreatic cells. DNA molecules having coding sequences substantially the same as the coding sequence shown in FIGS. 1A–1D (SEQ ID NO. 1) may be used as the oligonucleotides of the pharmaceutical composition.

This invention also provides a method of treating abnormalities which are alleviated by reduction of expression of a betaine/GABA transporter. This method comprises administering to a subject an effective amount of the pharmaceutical composition described above effective to reduce expression of the betaine/GABA transporter by the subject. This invention further provides a method of treating an abnormal condition related to betaine/GABA transporter activity which comprises administering to a subject an amount of the pharmaceutical composition described above effective to reduce expression of the betaine/GABA transporter by the subject. Examples of such abnormal conditions are epilepsy, migraine, ischemia, myoclonus, spasticity, and chronic pain.

Antisense oligonucleotide drugs inhibit translation of mRNA encoding these transporters. Synthetic antisense oligonucleotides, or other antisense chemical structures are designed to bind to mRNA encoding a betaine/GABA transporter and are useful as drugs to inhibit expression of betaine/GABA transporter genes in patients. This invention provides a means to therapeutically alter levels of expression of a mammalian betaine/GABA transporters by the use of a synthetic antisense oligonucleotide drug (SAOD) which inhibits translation of mRNA encoding these transporters. Synthetic antisense oligonucleotides, or other antisense chemical structures designed to recognize and selectively bind to mRNA, are constructed to be complementary to portions of the nucleotide sequence shown in FIGS. 1A–1D (SEQ ID NO. 1) of DNA, RNA or of chemically modified, artificial nucleic acids. The SAOD is designed to be stable in the blood stream for administration to patients by injection, or in laboratory cell culture conditions, for administration to cells removed from the patient. The SAOD is designed to be capable of passing through cell membranes in order to enter the cytoplasm of the cell by virtue of physical and chemical properties of the SAOD which render it capable of passing through cell membranes (e.g., by designing small, hydrophobic SAOD chemical structures) or by virtue of specific transport systems in the cell which recognize and transport the SAOD into the cell. In addition, the SAOD can be designed for administration only to certain selected cell populations by targeting the SAOD to be recognized by specific cellular uptake mechanisms which bind and take up the SAOD only within certain selected cell populations. For example, the SAOD may be designed to bind to a transporter found only in a certain cell type, as discussed above. The SAOD is also designed to recognize and selectively bind to the target mRNA sequence, which may correspond to a sequence contained within the sequence shown in FIGS. 1A–1D (SEQ ID NO. 1) by virtue of complementary base pairing to the mRNA. Finally, the SAOD is designed to inactivate the target mRNA sequence by any of three mechanisms: 1) by binding to the target mRNA and thus inducing degradation of the mRNA by intrinsic cellular mechanisms such as RNAse I digestion, 2) by inhibiting translation of the mRNA target by interfering with the binding of translation-regulating factors or of ribosomes, or 3) by inclusion of other chemical structures, such as ribozyme sequences or reactive chemical groups, which either degrade or chemically modify the target mRNA. Synthetic antisense oligonucleotide drugs have been shown to be capable of the properties described above when directed against mRNA targets (Cohen, J. S., 1989; Weintraub, H. M., 1990). In addition, coupling of ribozymes to antisense oligonucleotides is a promising strategy for inactivating target mRNA (N. Sarver et al. 1990). An SAOD serves as an effective therapeutic agent if it is designed to be administered to a patient by injection, or if the patient's target cells are removed, treated with the SAOD in the laboratory, and replaced in the patient. In this manner, an SAOD serves as a therapy to reduce transporter expression in particular target cells of a patient, in any clinical condition which may benefit from reduced expression of GABA or taurine transporters.

This invention provides an antibody directed to the mammalian betaine/GABA transporter. This antibody may comprise, for example, a monoclonal antibody directed to an epitope of a mammalian betaine/GABA transporter present on the surface of a cell, the epitope having an amino acid sequence substantially the same as the amino acid sequence for a cell surface epitope of the human betaine/GABA transporter included in the amino acid sequence shown in FIGS. 1A–1D (SEQ ID NOs. 1 and 3). This invention provides an antibody directed to a human betaine/GABA transporter. This antibody may comprise, for example, a monoclonal antibody directed to an epitope of a human betaine/GABA transporter present on the surface of a cell, the epitope having an amino acid sequence substantially the same as an amino acid sequence for a cell surface epitope of the human betaine/GABA transporter included in the amino acid sequence shown in FIGS. 1A–1D (SEQ ID NOs. 1 and 3). Amino acid sequences may be analyzed by methods well known to those skilled in the art to determine whether they produce hydrophobic or hydrophilic regions in the proteins which they build. In the case of cell membrane proteins, hydrophobic regions are well known to form the part of the protein that is inserted into the lipid bilayer which forms the cell membrane, while hydrophilic regions are located on the cell surface, in an aqueous environment. Therefore, antibodies directed to hydrophilic amino acid sequences specific to a human transporter will bind to a surface epitope of a human taurine transporter and antibodies directed to the conserved hydrophilic amino acid sequences shown in FIGS. 1A–1D (SEQ ID NOs. 1 and 3) will bind to a surface epitope of a mammalian betaine/GABA transporter. Antibodies directed to mammalian or human transporters may be serum-derived or monoclonal and are prepared using methods well known in the art. For example, monoclonal antibodies are prepared using hybridoma technology by fusing antibody producing B cells from immunized animals with myeloma cells and selecting the resulting hybridoma cell line producing the desired antibody. Cells such as NIH3T3 cells or Ltk⁻ cells may be used as immunogens to raise such an antibody. Alternatively, synthetic peptides may be prepared using commercially available machines and the amino acid sequences shown in FIGS. 1A–1D (SEQ ID NOs 1 and 2). As a still further alternative, DNA, such as a cDNA or a fragment thereof, may be cloned and expressed and the resulting polypeptide recovered and used as an immunogen. These antibodies are useful to detect the presence of mammalian transporters encoded by the isolated DNA, or to inhibit the function of the transporters in living animals, in humans, or in biological tissues or fluids isolated from animals or humans.

This invention also provides a pharmaceutical composition which comprises an effective amount of an antibody directed to an epitope of the mammalian transporter, effective to block binding of naturally occurring substrates to the transporter, and a pharmaceutically acceptable carrier. A monoclonal antibody directed to a comserved epitope of a human betaine/GABA transporter present on the surface of a cell which has an amino acid sequence substantially the same as an amino acid sequence for a cell surface epitope of the human betaine/GABA transporter included in the amino acid sequences shown in FIGS. 1A–1D (SEQ ID NOs. 1 and 3) is useful for this purpose.

This invention also provides a pharmaceutical composition which comprises an effective amount of an antibody directed to an epitope of the human betaine/GABA transporter, effective to block binding of naturally occurring substrates to the human betaine/GABA transporter, and a pharmaceutically acceptable carrier. A monoclonal antibody directed to an epitope of a human betaine/GABA transporter present on the surface of a cell which has an amino acid sequence substantially the same as an amino acid sequence for a cell surface epitope of the human betaine/GABA transporter included in the amino acid sequences shown in FIGS. 1A–1D (SEQ ID NOs. 1 and 3) is useful for this purpose.

This invention also provides a method of treating abnormalities in a subject which are alleviated by reduction of expression of a mammalian betaine/GABA transporter which comprises administering to the subject an effective amount of the pharmaceutical composition described above effective to block binding of naturally occurring substrates to the mammalian betaine/GABA transporter and thereby alleviate abnormalities resulting from overexpression of the mammalian betaine/GABA transporter. This invention also provides a pharmaceutical composition which comprises an effective amount of an antibody directed to an epitope of a human betaine/GABA transporter, effective to block binding of naturally occurring substrates to the human betaine/GABA transporter, and a pharmaceutically acceptable carrier. A monoclonal antibody directed to a conserved epitope specific to a betaine/GABA transporter present on the surface of a cell which has an amino acid sequence substantially the same as an amino acid sequence for a cell surface epitope of the human betaine/GABA transporter included in the amino acid sequence shown in FIGS. 1A–1D (SEQ ID NOs. 1 and 3) is useful for this purpose. Binding of the antibody to the transporter prevents the transporter from functioning, thereby neutralizing the effects of overexpression. The monoclonal antibodies described above are both useful for this purpose. This invention additionally provides a method of treating an abnormal condition related to an excess of transporter activity which comprises administering to a subject an amount of the pharmaceutical composition described above effective to block binding of naturally occurring substrates to the transporter and thereby alleviate the abnormal condition. Some examples of abnormal conditions associated with abnormal betaine/GABA transporter activity are epilepsy, migraine, ischemia, myoclonus, spasticity, and the treatment of chronic pain.

This invention provides methods of detecting the presence of a betaine/GABA transporter on the surface of a cell which comprises contacting the cell with an antibody directed to the mammalian betaine/GABA transporter or an antibody directed to the human betaine/GABA transporter, under conditions permitting binding of the antibody to the transporter, detecting the presence of the antibody bound to the cell, and thereby the presence of the mammalian betaine/GABA transporter or the human betaine/GABA transporter on the surface of the cell. Such methods are useful for determining whether a given cell is defective in expression of betaine/GABA transporter on the surface of the cell. Bound antibodies are detected by methods well known in the art, for example by binding fluorescent markers to the antibodies and examining the cell sample under a fluorescence microscope to detect fluorescence on a cell indicative of antibody binding. The monoclonal antibodies described above are useful for this purpose.

This invention provides a transgenic nonhuman mammal expressing DNA encoding a mammalian betaine/GABA transporter. This invention further provides a transgenic nonhuman mammal expressing DNA encoding a human betaine/GABA transporter. This invention also provides a transgenic nonhuman mammal expressing DNA encoding a mammalian betaine/GABA transporter so mutated as to be incapable of normal transporter activity and not expressing native betaine/GABA transporter activity. This invention further provides a transgenic nonhuman mammal expressing DNA encoding a human betaine/GABA transporter so mutated as to be incapable of normal transporter activity, and not expressing native betaine/GABA transporter.

This invention provides a transgenic nonhuman mammal whose genome comprises DNA encoding a mammalian betaine/GABA transporter so placed as to be transcribed into antisense mRNA which is complementary to mRNA encoding the betaine/GABA transporter and which hybridizes to mRNA encoding the betaine/GABA transporter thereby reducing its translation. This invention further provides a transgenic nonhuman mammal whose genome comprises DNA encoding a human betaine/GABA transporter so placed as to be transcribed into antisense mRNA which is complementary to mRNA encoding a betaine/GABA transporter and which hybridizes to mRNA encoding a betaine/GABA transporter thereby reducing its translation. The DNA may additionally comprise an inducible promoter or additionally comprise tissue specific regulatory elements, so that expression can be induced, or restricted to specific cell types. Examples of DNA are DNA or cDNA molecules having a coding sequence substantially the same as the coding sequences shown in FIGS. 1A–1D (SEQ ID NOs. 1). An example of a transgenic animal is a transgenic mouse. Examples of tissue specificity-determining regions are the metallothionein promotor (Low et al., 1986,) and the L7 promotor (Oberdict et al. 1990).

Animal model systems which elucidate the physiological and behavioral roles of mammalian transporters are produced by creating transgenic animals in which the expression of a transporter is either increased or decreased, or the amino acid sequence of the expressed transporter protein is altered, by a variety of techniques. Examples of these techniques include, but are not limited to: 1) Insertion of normal or mutant versions of DNA encoding a mammalian transporter or homologous animal versions of these genes, by microinjection, retroviral infection or other means well known to those skilled in the art, into appropriate fertilized embryos in order to produce a transgenic animal (Hogan et al., 1986) Homologous recombination (Cappechi, M. R., 1989; Zimmer A., and Gruss, P., 1989) of mutant or normal, human or animal versions of these genes with the native gene locus in transgenic animals to alter the regulation of expression or the structure of these transporters. The technique of homologous recombination is well known in the art. It replaces the native gene with the inserted gene and so is useful for producing an animal that cannot express native transporter but does express, for example, an inserted mutant transporter, which has replaced the native transporter in the animal's genome by recombination, resulting in underexpression of the transporter. Microinjection adds genes to the genome, but does not remove them, and so is useful for producing an animal which expresses its own and added transporters, resulting in overexpression of the transporter.

One means available for producing a transgenic animal, with a mouse as an example, is as follows: Female mice are mated, and the resulting fertilized eggs are dissected out of their oviducts. The eggs are stored in an appropriate medium such as M2 medium (Hogan et al. 1986). DNA or cDNA encoding a human betaine/GABA transporter is purified from a vector (such as plasmid pcEXV-hBGT, ATCC Accession No. 75393, deposited Dec. 30, 1992, described above) by methods well known in the art. Inducible promoters may be fused with the coding region of the DNA to provide an experimental means to regulate expression of the trans-gene. Alternatively or in addition, tissue specific regulatory elements may be fused with the coding region to permit tissue-specific expression of the trans-gene. The DNA, in an appropriately buffered solution, is put into a microinjection needle (which may be made from capillary tubing using a pipet puller) and the egg to be injected is put in a depression slide. The needle is inserted into the pronucleus of the egg, and the DNA solution is injected. The injected egg is then transferred into the oviduct of a pseudopregnant mouse (a mouse stimulated by the appropriate hormones to maintain pregnancy but which is not actually pregnant), where it proceeds to the uterus, implants, and develops to term. As noted above, microinjection is not the only method for inserting DNA into the egg cell, and is used here only for exemplary purposes.

Since the normal action of transporter-specific drugs is to activate or to inhibit the transporter, the transgenic animal model systems described above are useful for testing the biological activity of drugs directed against these transporters even before such drugs become available. These animal model systems are useful for predicting or evaluating possible therapeutic applications of drugs which activate or inhibit these transporters by inducing or inhibiting expression of the native or trans-gene and thus increasing or decreasing expression of normal or mutant transporters in the living animal. Thus, a model system is produced in which the biological activity of drugs directed against these transporters are evaluated before such drugs become available. The transgenic animals which over or under produce the transporter indicate by their physiological state whether over or under production of the transporter is therapeutically useful. It is therefore useful to evaluate drug action based on the transgenic model system. One use is based on the fact that it is well known in the art that a drug such as an antidepressant acts by blocking neurotransmitter uptake, and thereby increases the amount of neurotransmitter in the synaptic cleft. The physiological result of this action is to stimulate the production of less transporter by the affected cells, leading eventually to underexpression. Therefore, an animal which underexpresses transporter is useful as a test system to investigate whether the actions of such drugs which result in under expression are in fact therapeutic. Another use is that if overexpression is found to lead to abnormalities, then a drug which down-regulates or acts as an antagonist to the transporter is indicated as worth developing, and if a promising therapeutic application is uncovered by these animal model systems, activation or inhibition of the GABA transporter is achieved therapeutically either by producing agonist or antagonist drugs directed against these GABA transporters or by any method which increases or decreases the expression of these transporters in man.

Further provided by this invention is a method of determining the physiological effects of expressing varying levels of a mammalian betaine/GABA transporter which comprises producing a transgenic nonhuman animal whose levels of mammalian betaine/GABA transporter expression are varied by use of an inducible promoter which regulates transporter expression. This invention also provides a method of determining the physiological effects of expressing varying levels of mammalian Betaine/GABA transporter which comprises producing a panel of transgenic nonhuman animals each expressing a different amount of the mammalian betaine\GABA transporter. Such animals may be produced by introducing different amounts of DNA encoding a mammalian betaine/GABA transporter into the oocytes from which the transgenic animals are developed.

This invention provides a method of determining the physiological effects of expressing varying levels of a human betaine/GABA transporter which comprises producing a transgenic nonhuman animal whose levels of human betaine/GABA transporter expression are varied by use of an inducible promoter which regulates transporter expression. This invention also provides a method of determining the physiological effects of expressing varying levels of a human betaine/GABA transporter which comprises producing a panel of transgenic nonhuman animals each expressing a different amount of the human betaine/GABA transporter. Such animals may be produced by introducing different amounts of DNA encoding a human betaine/GABA transporter into the oocytes from which the transgenic animals are developed.

This invention also provides a method for identifying a substance capable of alleviating abnormalities resulting from overexpression of a mammalian betaine/GABA transporter comprising administering the substance to a transgenic nonhuman mammal expressing at least one artificially introduced DNA molecule encoding a mammalian betaine/GABA transporter and determining whether the substance alleviates the physical and behavioral abnormalities displayed by the transgenic nonhuman mammal as a result of overexpression of the mammalian betaine/GABA transporter. This invention also provides a method for identifying a substance capable of alleviating abnormalities resulting from overexpression of a human transporter comprising administering the substance to a transgenic nonhuman mammal expressing at least one artificially introduced DNA molecule encoding a human betaine/GABA transporter and determining whether the substance alleviates the physical and behavioral abnormalities displayed by the transgenic nonhuman mammal as a result of overexpression of a human betaine/GABA transporter. As used herein, the term "substance" means a compound or composition which may be natural, synthetic, or a product derived from screening. Examples of DNA molecules are DNA or cDNA molecules having a coding sequence substantially the same as the coding sequences shown in FIGS. 1A–1D (SEQ ID NO. 1).

This invention provides a pharmaceutical composition comprising an amount of the substance described supra effective to alleviate the abnormalities resulting from overexpression of a mammalian betaine/GABA transporter and a pharmaceutically acceptable carrier. This invention also provides a pharmaceutical composition comprising an amount of the substance described supra effective to alleviate the abnormalities resulting from overexpression of a human betaine/GABA transporter and a pharmaceutically acceptable carrier.

This invention also provides a method for treating the abnormalities resulting from overexpression of a mammalian betaine/GABA transporter which comprises administering to a subject an amount of the pharmaceutical composition described above effective to alleviate the abnormalities resulting from overexpression of a mammalian betaine/GABA transporter. This invention further provides a method for treating the abnormalities resulting from overexpression of a human betaine/GABA transporter which comprises administering to a subject an amount of the pharmaceutical composition described above effective to alleviate the abnormalities resulting from overexpression of the human betaine/GABA transporter.

This invention provides a method for identifying a substance capable of alleviating the abnormalities resulting from underexpression of a mammalian betaine/GABA transporter comprising administering the substance to the transgenic nonhuman mammal described above which expresses only nonfunctional mammalian transporter and determining whether the substance alleviates the physical and behavioral abnormalities displayed by the transgenic nonhuman mammal as a result of underexpression of a mammalian betaine/GABA transporter. This invention further provides a method for identifying a substance capable of alleviating the abnormalities resulting from underexpression of a human betaine/GABA transporter comprising administering the substance to the transgenic nonhuman mammal described above which expresses only nonfunctional human betaine/GABA and determining whether the substance alleviates the physical and behavioral abnormalities displayed by the transgenic nonhuman mammal as a result of underexpression of a human betaine/GABA.

This invention also provides a pharmaceutical composition comprising an amount of a substance effective to alleviate abnormalities resulting from underexpression of a mammalian betaine/GABA transporter and a pharmaceutically acceptable carrier. This invention also provides a pharmaceutical composition comprising an amount of a substance effective to alleviate abnormalities resulting from underexpression of a human betaine/GABA and a pharmaceutically acceptable carrier.

This invention provides a method for treating the abnormalities resulting from underexpression of a mammalian betaine/GABA transporter which comprises administering to a subject an amount of the pharmaceutical composition described above effective to alleviate the abnormalities resulting from underexpression of a mammalian betaine/GABA transporter. This invention further provides a method for treating the abnormalities resulting from underexpression of a human betaine/GABA transporter which comprises administering to a subject an amount of the pharmaceutical composition described above effective to alleviate the abnormalities resulting from underexpression of a human betaine/GABA transporter.

This invention provides a method for diagnosing a predisposition to a disorder associated with the expression of a specific mammalian betaine/transporter allele which comprises: a) obtaining DNA of subjects suffering from the disorder; b) performing a restriction digest of the DNA with a panel of restriction enzymes; c) electrophoretically separating the resulting DNA fragments on a sizing gel; d) contacting the resulting gel with a nucleic acid probe capable of specifically hybridizing to DNA encoding a mammalian betaine/GABA transporter and labelled with a detectable marker; e) detecting labelled bands which have hybridized to the DNA encoding a mammalian betaine/GABA transporter labelled with a detectable marker to create a unique band pattern specific to the DNA of subjects suffering from the disorder; f) preparing DNA obtained for diagnosis by steps a–e; and g) comparing the unique band pattern specific to the DNA of subjects suffering from the disorder from step e and the DNA obtained for diagnosis from step f to determine whether the patterns are the same or different and thereby to diagnose predisposition to the disorder if the patterns are the same. This method may also be used to diagnose a disorder associated with the expression of a specific mammalian betaine/GABA transporter allele.

This invention provides a method for diagnosing a predisposition to a disorder associated with the expression of a specific human betaine/GABA transporter allele which comprises: a) obtaining DNA of subjects suffering from the disorder; b) performing a restriction digest of the DNA with a panel of restriction enzymes; c) electrophoretically separating the resulting DNA fragments on a sizing gel; d) contacting the resulting gel with a nucleic acid probe capable of specifically hybridizing to DNA encoding a human betaine/GABA transporter and labelled with a detectable marker; e) detecting labelled bands which have hybridized to the DNA encoding a human betaine/GABA labelled with a detectable marker to create a unique band pattern specific to the DNA of subjects suffering from the disorder; f) preparing DNA obtained for diagnosis by steps a–e; and g) comparing the unique band pattern specific to the DNA of subjects suffering from the disorder from step e and the DNA obtained for diagnosis from step f to determine whether the patterns are the same or different and thereby to diagnose predisposition to the disorder if the patterns are the same. This method may also be used to diagnose a disorder associated with the expression of a specific human betaine/GABA transporter allele.

This invention provides a method of preparing an isolated betaine/GABA transporter which comprises inducing cells to express transporter, recovering the transporter from the resulting cells, and purifying the transporter so recovered. An example of an isolated betaine/GABA transporter is an isolated protein having substantially the same amino acid sequence as the amino acid sequence shown in FIGS. 1A–1D (SEQ ID NO. 1). This invention further provides a method for preparing an isolated human GABA transporter which comprises inducing cells to express the human betaine/GABA transporter, recovering the human betaine/GABA transporter from the resulting cells, and purifying the human betaine/GABA transporter so recovered. An example of an isolated human betaine/GABA transporter is an isolated protein having substantially the same amino acid sequence as the amino acid sequence shown in FIGS. 1A–1D (SEQ ID NOs. 1 and 3). For example, cells can be induced to express transporters by exposure to substances such as hormones. The cells can then be homogenized and the betaine/GABA transporter isolated from the homogenate using an affinity column comprising, for example, GABA, betaine or another substance which is known to bind to the betaine/GABA transporter. The resulting fractions can then be purified by contacting them with an ion exchange column, and determining which fraction contains betaine/GABA transporter activity or binds anti-betaine/GABA transporter antibodies.

This invention provides a method of preparing the isolated mammalian betaine/GABA transporter which comprises inserting nucleic acid encoding the mammalian betaine\GABA transporter in a suitable vector, inserting the resulting vector in a suitable host cell, recovering the transporter produced by the resulting cell, and purifying the transporter so recovered. An example of an isolated betaine/GABA transporter is an isolated protein having substantially the same amino acid sequence as the amino acid sequence shown in FIGS. 1A–1D (SEQ ID Nos 1 and 3). This invention also provides a method of preparing the isolated human betaine/GABA transporter which comprises inserting nucleic acid encoding a human betaine/GABA transporter in a suitable vector, inserting the resulting vector in a suitable host cell, recovering the transporter produced by the resulting cell, and purifying the transporter so recovered. These methods for preparing mammalian or human betaine/GABA transporter uses recombinant DNA technology methods well known in the art. For example, isolated nucleic acid encoding a mammalianm or human betaine/GABA transporter is inserted in a suitable vector, such as an expression vector. A suitable host cell, such as a bacterial cell, or a eukaryotic cell such as a yeast cell, is transfected with the vector. Betaine/GABA transporter is isolated from the culture medium by affinity purification or by chromatography or by other methods well known in the art.

This invention provides a method for determining whether a compound not known to be capable of binding to a mammalian betaine/GABA transporter can bind to the mammalian betaine/GABA transporter which comprises contacting a mammalian cell comprising a DNA molecule encoding a mammalian betaine/GABA transporter with the compound under conditions permitting binding of compounds known to bind to the transporter, detecting the presence of any of the compound bound to the betaine/GABA transporter, and thereby determining whether the substrate binds to the betaine/GABA transporter.

This invention provides a method for determining whether a compound not known to be capable of binding to a human betaine/GABA transporter can bind to the human betaine/GABA transporter which comprises contacting a mammalian cell comprising a DNA molecule encoding a human betaine/GABA transporter with the compound under conditions permitting binding of compounds known to bind to the transporter, detecting the presence of any of the compound bound to the betaine/GABA transporter, and thereby determining whether the substrate binds to the betaine/GABA transporter. The DNA in the cell may have a coding sequence substantially the same as the coding sequences shown in FIGS. 1A–1D (SEQ ID NO 1). Preferably, the mammalian cell is nonneuronal in origin. An example of a nonneuronal mammalian cell is a Cos7 cell or an L tk– cell. The preferred method for determining whether a compound is capable of binding to a mammalian or a human betaine/GABA transporter comprises contacting a transfected nonneuronal mammalian cell (i.e. a cell that does not naturally express any type of transporter, thus will only express such a transporter if it is transfected into the cell) expressing a transporter on its surface, or contacting a membrane preparation derived from such a transfected cell, with the substrate under conditions which are known to prevail, and thus to be associated with, in vivo binding of the substrates to a transporter, detecting the presence of any of the substrate being tested bound to the transporter on the surface of the cell, and thereby determining whether the substrate binds to the transporter. This response system is obtained by transfection of isolated DNA into a suitable host cell. Such a host system might be isolated from pre-existing cell lines, or can be generated by inserting appropriate components into existing cell lines. Such a transfection system provides a complete response system for investigation or assay of the functional activity of mammalian transporters with substrates as described above. Transfection systems are useful as living cell cultures for competitive binding assays between known or candidate drugs and substrates which bind to the transporter and which are labeled by radioactive, spectroscopic or other reagents. Membrane preparations containing the transporter isolated from transfected cells are also useful for these competitive binding assays. A transfection system constitutes a "drug discovery system" useful for the identification of natural or synthetic compounds with potential for drug development that can be further modified or used directly as therapeutic compounds to activate or inhibit the natural functions of the mammalian transporter and/or the human transporter. The transfection system is also useful for determining the affinity and efficacy of known drugs at the mammalian transporter sites and human transporter sites.

This invention also provides a method of screening drugs to identify drugs which specifically interact with, and bind to, the mammalian betaine/GABA transporter on the surface of a cell which comprises contacting a mammalian cell comprising a DNA molecule encoding a mammalian betaine/GABA transporter on the surface of a cell with a plurality of drugs, detecting those drugs which bind to the mammalian cell, and thereby identifying drugs which specifically interact with, and bind to, the mammalian betaine/GABA transporter. This invention also provides a method of screening drugs to identify drugs which specifically interact with, and bind to, a human betaine/GABA transporter on the surface of a cell which comprises contacting a mammalian cell comprising a DNA molecule encoding a human betaine/GABA transporter on the surface of a cell with a plurality of drugs, detecting those drugs which bind to the mammalian cell, and thereby identifying drugs which specifically interact with, and bind to, the human betaine/GABA transporter. The DNA in the cell may have a coding sequence substantially the same as the coding sequences shown in FIGS. 1A–1D (SEQ ID NO. 1). Various methods of detection may be employed. The drugs may be "labeled" by association with a detectable marker substance (e.g., radiolabel or a non-isotopic label such as biotin). Preferably, the mammalian cell is nonneuronal in origin. An example of a nonneuronal mammalian cell is a Cos7 cell or an L tk– cell. Drug candidates are identified by choosing chemical compounds which bind with high affinity to the expressed transporter protein in transfected cells, using radioligand binding methods well known in the art, examples of which are shown in the binding assays described herein. Drug candidates are also screened for selectivity by identifying compounds which bind with high affinity to one particular transporter subtype but do not bind with high affinity to any other transporter subtype or to any other known transporter site. Because selective, high affinity compounds interact primarily with the target transporter site after administration to the patient, the chances of producing a drug with unwanted side effects are minimized by this approach. This invention provides a pharmaceutical composition comprising a drug identified by the method described above and a pharmaceutically acceptable carrier. As used herein, the term "pharmaceutically acceptable carrier" encompasses any of the standard pharmaceutical carriers, such as a phosphate buffered saline solution, water, and emulsions, such as an oil/water or water/oil emulsion, and various types of wetting agents. Once the candidate drug has been shown to be adequately bio-available following a particular route of administration, for example orally or by injection (adequate therapeutic concentrations must be maintained at the site of action for an adequate period to gain the desired therapeutic benefit), and has been shown to be non-toxic and therapeutically effective in appropriate disease models, the drug may be administered to patients by that route of administration determined to make the drug bio-available, in an appropriate solid or solution formulation, to gain the desired therapeutic benefit.

Applicants have identified a human betaine/GABA transporter and have described methods for the identification of pharmacological compounds for therapeutic treatments. Pharmacological compounds which are directed against specific transporter subtypes provide effective new therapies with minimal side effects.

Elucidation of the molecular structures of the betaine/GABA transporter is an important step in the understanding of GABAergic neurotransmission. This disclosure reports the isolation, amino acid sequence, and functional expression of a DNA clone from human brain which encodes a betaine/GABA transporter. The identification of this betaine/GABA transporter will play a pivotal role in elucidating the molecular mechanisms underlying GABAergic transmission, and should also aid in the development of novel therapeutic agents.

Complementary DNA clones (designated hS1a, hS13a, hS26a and hS38a) encoding betaine/GABA transporters have been isolated from human brain, and their functional properties have been examined in mammalian cells. The nucleotide sequence of hS1a predicts a protein of 614 amino acids with 12 highly hydrophobic regions compatible with membrane-spanning domains. When incubated with 50 nM [$^3$H]GABA, COS cells transiently transfected with hS1a accumulated approximately 10-fold greater radioactivity as non-transfected control cells. In stable LM tk– cell lines expressing hS1a, a 92 fold enhancement of [$^3$H]GABA uptake was observed, compared to non-transfected cells.

Analysis of the betaine/GABA transporter structure and function provides a model for the development of drugs useful for the treatment of epilepsy, migraine, ischemia, myoclonus, spasticity, and chronic pain.

This invention identifies for the first time a betaine/GABA transporter protein, its amino acid sequence, and its human gene. The information and experimental tools provided by this discovery are useful to generate new therapeutic agents, and new therapeutic or diagnostic assays for this new transporter protein, its associated mRNA molecules or its associated genomic DNAs. The information and experimental tools provided by this discovery will be useful to generate new therapeutic agents, and new therapeutic or diagnostic assays for this new transporter protein, its associated mRNA molecules, or its associated genomic DNAs.

Specifically, this invention relates to the first isolation of cDNAs encoding a betaine/GABA. In addition, the human betaine/GABA transporter and has been expressed in Cos7 cells and LM tk– cell by transfecting the cells with the plasmid containing DNA encoding the human betaine/GABA transporter. The pharmacological binding properties of the encoded betaine/GABA has been determined, and its binding properties classify this protein as betaine/GABA transporter. Mammalian cell lines expressing the human betaine/GABA transporter on the cell surface have been constructed, thus establishing the first well-defined, cultured cell lines with which to study the betaine/GABA transporter.

This invention further provides a method of treating an abnormal condition such as epilepsy, migraine, ischemia, myoclonus, spasticity or chronic pain. The abnormal condition may be associated with overexpression or underexpression of the betaine/GABA trasnporter or may be associated with the presence of excess or deficient amounts of naturally occuring substrates, the transport of which is controlled by the betaine/GABA transporter. In the case of overexpression of the transporter, the abnormal condition may be treated by administering, in the form of pharmaceutical composition, a ligand which specifically binds to the betaine/GABA transporter and inhibits the transport of a naturally occuring substrate. In the case of underexpression, the abnormal condition may be treated by administering, in the form of a pharmaceutical composition, a ligand which specifically binds to the transporter and enhances the transport of a natural occuring substrate. In the case of an excess amount of a naturally occuring substrate the abnormal condition may be treated by administering a ligand which conpetitively inhibits binding, and thus transport, pf the natural occuring substrate. Finally, in the case of a deficient amount of a naturally occuring substrate the abnormal condition may be treated by either administering a ligand which enhances binding or transport of the natural occuring substrate or binds to the transporter and mimics the biological function of the natural occuring substrate. In all cases the ligand is present in a pharmaceutical acceptable carrier in an amount effective to accomplish the desired effect.

This invention will be better understood by reference to the Experimental Details which follow, but those skilled in the art will readily appreciate that the specific experiments detailed are only illustrative, and are not meant to limit the invention as described herein, which is defined by the claims which follow thereafter.

MATERIALS and METHODS

Use of PCR to Identify cDNA Libraries for Screening: Degenerate primers were designed to amplify putative human GAT-2 cDNA clones based on sequence comparisons between conserved regions of several transporters. The sequences of the degenerate primers were 5'-TGGAATTCG(G/C)CAA(C/T)GTTTGG(C/A)GTTT(C/T)CCTTA (sense) and 5'-TCGCGGCCGCAA(A/G)AAGATCTGTGTTGCIGC(A/G)TC (antisense). PCR reactions were carried out in a buffer containing 20 mM Tris (pH 8.3), 50 mM KCl, 1.5 mM MgCl$_2$, 0.001% gelatin, 2 mM dNTP's, 1 µM each primer, Taq polymerase, and an aliquot of a lambda phage library, water, or a control plasmid for 40 cycles of 94° C. for 2 min., 40° C. for 2 min., and 72° C. for 3 min. PCR products were separated by electrophoresis in 1.2% agarose gels, blotted to nylon membranes (Genescreen Plus; New England Nuclear, Boston, Mass.), and hybridized at high stringency overnight with $^{32}$P-labeled probes representing the rat GAT-2 sequence (overlapping 45 mers: sense, 5'-GTCCTGAAGATCTCAG-ATGGCATCCAGCACCTGGGGTCCCTGCGC; antisense, 5'-GCAGGAGGCACAGGACCAGCTCCCAGCGCAGG-GACCCCAGGTGCT). Hybridization was at 40° C. in a solution containing 50% formamide, 10% dextran sulfate, 5× SSC, 1× Denhardt's, and 100 µg/ml of sonicated salmon sperm DNA. Blots were washed at high stringency (0.1× SSC, 50° C.) and exposed to Kodak XAR film overnight with one intensifying screen at –70° C.

Isolation and Sequencing of Human Betaine/GABA cDNA Clones: A human striatum cDNA library in the Lambda ZAP II vector (Stratagene, La Jolla, Calif.) identified by PCR hybridization; 0.1× SSC, 50° C. wash) with the rat GAT-2 probes described above. Hybridizing lambda phage were plaque purified and converted to phagemids by in vivo excision with f1 helper phage. Nucleotide sequences of double-stranded cDNAs in pBluescript were analyzed by the Sanger dideoxy nucleotide chain-termination method (Sanger, 1977) using Sequenase (U.S. Biochemical Corp., Cleveland, Ohio). A cDNA clone (designated hS1a) identified as representing the entire coding region of a novel human transporter was subcloned into a eukaryotic expression vector (modified from pcEXV-3, Miller and Germain, 1986) as a 3.1 Kb XbaI/SalI fragment.

Transfection: Transient transfections of COS cells were carried out using DEAE-dextran with DMSO according to the method of Lopata et al. (1984), with minor modifications. Stable cell lines were produced in LMtk– cells using calcium phosphate precipitation, and selected by their resistance to G-418 resistance, as previously described (Adham et al., 1992). Similar results were obtained with transient and stable transfectants.

Transport Studies: Transport of [$^3$H]GABA was measured in both attached cells and in cells maintained in suspension culture. Transport in attached cells was measured as previously described (Smith et al., 1992). Briefly, COS cells grown in 24-well (well diameter=18 mm) plates were washed 3× with HEPES-buffered saline (HBS, in mM: NaCl, 150; HEPES, 20; CaCl$_2$, 1; glucose, 10; KCl, 5; MgCl$_2$, 1; pH 7.4) and allowed to equilibrate in a 37° C. water bath. After 10 minutes the medium was removed and a solution containing 50 nM [$^3$H]GABA and required drugs in HBS was added (0.5 ml/18 mm well). Non-specific uptake was defined in parallel wells with 1 mM unlabeled substrate, and was subtracted from total uptake (no competitor) to yield specific uptake; all data represent specific uptake. Plates were incubated at 37° C. for 10 minutes unless indicated otherwise, then washed rapidly 3× with ice-cold HBS. Cells were solubilized with 0.05% sodium deoxycholate/0.1N NaOH, an aliquot neutralized with 1N HCl, and radioactivity was determined by scintillation counting. Protein was quantified in an aliquot of the solubilized cells using a BIO-RAD protein assay kit, according to the manufacturers directions.

Transport was also measured in suspension. The details of this method will described in detail in a subsequent publication (Borden et al., manuscript in preparation). Briefly, transient (COS-7) or stable (LM) transfectants were removed from culture plates with trypsin/EDTA, and transferred to suspension culture. The cells were grown in a temperature-controlled shaking incubator, using a medium containing methylcellulose. To measure transport the cells were washed by centrifugation, and resuspended in HBS. The assay was performed in 96-well microtiter plates (total volume=0.25 ml/well). The cells were incubated with 50 nM [$^3$H]GABA and required drugs for 10 minutes at 37° C., then collected using a Brandel harvester. Cell-associated radioactivity retained on the filters was determined by scintillation counting.

Materials: [$^3$H]GABA (sp. activity≈90 Ci/mmole) was obtained from New England Nuclear (Boston, Mass.). β-alanine, betaine and L-DABA (L-(2,4)diaminobutyric acid) were from Sigma Chemical Company (St. Louis, Mo.); guvacine, nipecotic acid, and OH-nipecotic (hydroxynipecotic acid) were from RBI (Natick, Mass.). ACHC (cis-3-aminocyclohexanecarboxylic acid) was kindly provided by Research Biochemicals Incorporated as part of the Chemical Synthesis Program of the National Institute of Mental Health, Contract 278-90-0007 (BS).

RESULTS

Cloning of the Human Betaine/GABA Transporter

With the aim of obtaining a cDNA clone encoding the human homologue of the rat GAT-2 GABA transporter (Borden et al., 1992), degenerate PCR primers were used to amplify transporter sequences from human cDNA libraries. Amplified sequences were detected in the libraries by hybridization at high stringency with radiolabeled rat GAT-2 oligonucleotides representing a portion of the putative second extracellular loop. The human striatum library (Stratagene) identified by this approach was screened at high-stringency with the same probes; positive plaques were purified by successive screening at high stringency. Four cDNA clones were isolated (hS1a, hS13a, hS26a, and hS38a) that exhibited significant homology with the nucleotide sequence of rat GAT-2 (71%), but were too dissimilar to represent species homologues of GAT-2. One of these, hS1a, was determined by sequence analysis to contain the full coding region of a transporter with 70% predicted amino acid identity with GAT-2. The complete nucleotide sequence and predicted amino acid sequence of hS1a are shown in FIGS. 1A–1D. In addition to 1842 base pairs of coding region, the sequence includes 5' and 3' untranslated sequence (210 and 165 base pairs, respectively). Translation of a long open reading frame predicts a protein of 614 amino acids with 12 putative transmembrane domains. While this work was in progress, a betaine/GABA transporter (BGT) was cloned from dog kidney (Yamauchi et al., 1992) that exhibited 91% amino acid identity with hS1a, a much closer degree of relationship than hS1a with the rat GAT-2. The nucleotide sequence of the untranslated regions of hS1a also shows a greater degree of identity with the dog BGT than with rat GAT-2, ≈65% vs. ≈35%, respectively. This comparison suggested that hS1a encoded a human betaine/GABA transporter distinct from GAT-2. Recently, a cDNA encoding a mouse brain GABA transporter was cloned by Lopez-Corcuera et al. (1992); the deduced amino acid sequence of this transporter is 88% identical to both the dog betaine/GABA transporter (Yamauchi et al., 1992) and to that encoded by hS1a. As will be shown below, these three clones exhibit similar pharmacological profiles; accordingly, we will refer to the transporter encoded by hS1a as hBGT (human betaine/GABA transporter).

Pharmacological Characterization of Human Betaine/GABA Transporter

To determine whether hS1a encodes a GABA transporter, COS-7 cells were transiently transfected and examined for their ability to accumulate [$^3$H]GABA. A representative experiment is shown in FIG. 2, in which it can be seen that transfection results in approximately a 10-fold increase in uptake, as compared with control (non-transfected) cells. The level of expression varied from experiment to experiment, but was typically about 10-fold greater than non-transfected cells. Stable cell lines expressing hS1a were generated in LMtk⁻ cells. The highest level of expression was observed in clone 3 (hS1a-3). In a representative experiment using attached cells, the specific accumulation of [$^3$H]GABA in non-transfected (control) cells was 55,352 cpm/mg protein, whereas that in hS1a-3 was 5,097,569 cpm/mg. This represents a 92-fold increase in specific transport. Thus, enhanced uptake of [$^3$H]GABA was observed with both transient and stable transfectants.

The $K_M$ for GABA in hS1a-3 (assayed in suspension) was determined to be 13.6±0.6 μM (n=4), indicating that hS1a encodes a high-affinity GABA transporter. To determine the pharmacological specificity of the GABA transporter encoded by hS1a, we tested a variety of compounds for their ability to inhibit the specific uptake of [$^3$H]GABA (Table 1). The $IC_{50}$ values estimated from the inhibition data are presented in Table 2; for comparison, data for similar clones obtained from dog kidney cells (Yamauchi et al., 1992) and mouse brain (Lopez-Corcuera et al., 1992) are also shown. In hS1a, the most potent inhibitor (except for GABA, see above) is quinidine, which displays an $IC_{50}$ of about 50 μM. β-alanine, betaine, and nipecotic acid are somewhat less potent, displaying estimated $IC_{50}$ values in the range of 150–250 μM. Hydroxynipecotic acid and guvacine are weak inhibitors (estimated $IC_{50}$>1,000 μM), as are ACHC and Tiagabine.

TABLE 1

Pharmacological Specificity of [$^3$H]GABA Uptake in Cells Expressing hS1a.

| Inhibitor | concentration | % Inhibition |
|---|---|---|
| ACHC | 100 μM | 0(1) |
| β-alanine | 100 μM | 42 ± 22(2) |
| betaine | 500 μM | 66 ± 15(3) |
| L-DABA | 100 μM | 24 ± 24(2) |
| guvacine | 100 μM | 5 ± 5(2) |
| OH-nipecotic | 100 μM | 8 ± 8(2) |
| nipecotic | 100 μM | 34 ± 19(2) |
| phloretin | 500 μM | 66(1) |
| quinidine | 100 μM | 92(1) |
| 500 μM | 85(1) | |
| (R)-Tiagabine | 100 μM | 12 ± 7(5) |

*COS-7 (transient transfection) or LMtk⁻ (stable; hS1a-3) cells were incubated for 10 minutes (37° C. with 50 nM [$^3$H]GABA and the indicated compounds. Non-specific uptake was determined with 1 mM GABA. Data show percent displacement of specific [$^3$H]GABA uptake, mean ± SEM (values in parentheses indicate number of experiments).

TABLE 2

Comparison of Betaine/GABA transporters from different species.

| | $IC_{50}$ (μM)[a] | | |
|---|---|---|---|
| Compound | human[b] | dog[c] | mouse[d] |
| GABA* | 14 | 93 | 79 |
| β-alanine | 138 | 2400 | 1900 |
| betaine | 258 | 398[f] | 206 |
| guvacine | 1900 | ND | 2800 |
| nipecotic acid | 194 | 4700 | 8000 |

TABLE 2-continued

Comparison of Betaine/GABA transporters from different species.

| Compound | IC$_{50}$ (μM)[a] | | |
|---|---|---|---|
| | human[b] | dog[c] | mouse[d] |
| OH-nipecotic acid | 1150 | ND | ND |
| phloretin | 258 | 200 | 37 |
| quinidine | 488 | 316 | 49 |

[a]The IC$_{50}$ values (concentration causing 50% inhibition) were estimated from data for one or two concentrations of inhibitor, using the equation % inhibition = L/(K$_i$ + L). The values are not corrected for the concentration of [$^3$H]GABA employed in the assay.
[b]data from Table 1
[c]data from Yamauchi et al., 1992
[d]data from Lopez-Corcuera et al., 1992
[e]data from full displacement curves
[f]data from saturation experiments using [$^{14}$C]betaine
ND = not determined

Discussion

In this communication we describe the cloning and expression of hS1a, a novel high-affinity GABA transporter from human brain. The sequence of hS1a is most identical to the betaine/GABA transporter cloned from dog kidney cells (Yamauchi et al. 1992), and to a related clone isolated from mouse brain (Lopez-Corcuera et al., 1992). These three clones also display similar, though not identical, pharmacological profiles. It should be pointed out that although the mouse clone was referred to as GAT-2 (Lopez-Corcuera et al., 1992), it is clearly distinct from the rat brain GAT-2 (Borden et al., 1992).

The differences in pharmacology of the three betaine/GABA transporters bear comment. It is noteworthy that GABA itself displays higher affinity at hBGT (K$_M$=13 μM) than at either the dog (K$_M$=93 μM) or mouse (K$_M$=79 μM) clones. This discrepancy probably reflects, at least in part, methodological differences. For example, the dog and mouse clones were expressed in oocytes, whereas we employed COS-7 or LMtk$^-$ fibroblasts for the human clone. Additionally, we measured transport for 10 minutes at 37° C., while the dog clone was assayed for 30 minutes at 25° C. (Yamauchi et al., 1992), and the mouse clone for 45 minutes (Lopez-Corcuera et al., 1992; temperature not reported by the authors). Another important factor is our use of suspension cultures. We have found that the affinity of GABA at GAT-1, GAT-2, and GAT-3 is increased about 10-fold when assayed in suspension, as compared to attached cells (Borden, unpublished). Under these conditions, the affinity of hS1a is about 5–10-fold lower than that of the human GAT-1 (Borden, unpublished), similar to results obtained with the mouse clones (Lopez-Corcuera et al., 1992; Liu et al., 1992a). Thus, when the different experimental conditions are taken into account, the affinity of hS1a relative to GAT-1 is similar to the affinity of the mouse and dog BGT relative to GAT-1.

It should also be noted that phloretin and quinidine are more potent at the mouse BGT than at the dog or human clones. Further, β-alanine and nipecotic acid are more potent at hS1a than at either of the other two transporters. The reason for these discrepancies is not known. We are currently generating full displacement curves for each of the inhibitors to further characterize this transporter. In addition, it will be necessary to examine the three clones under identical experimental conditions to determine whether the differences are methodological (see above), or actually reflect differences in the transporters. Last, it should be pointed out that the pharmacological profile of hBGT, in particular its sensitivity to β-alanine, is similar to that of GAT-2, GAT-3 (Borden et al., 1992), and the taurine transporter (Smith et al., 1992), but unlike that of GAT-1 (Guastella et al., 1990). Similarly, hS1a shows a higher degree of amino acid sequence identity to GAT-2 (70%), GAT-3 (66%), and the taurine transporter (61%), than to GAT-1 (51%). This cross-reactivity underscores the importance of understanding the action of therapeutic agents at all GABA transporters.

It is presently not clear whether the three betaine/GABA transporters are distinct genes, or species homologues of a single gene. Lopez-Corcuera al. (1992) speculated that the mouse and dog transporters are products of separate genes, based on the following observations: 1. The amino acid sequences of the two BGTs are only 88% identical, whereas the mouse (Liu et al., 1992a), rat (Guastella et al., 1990), and human (Nelson et al., 1990) GAT-1 exhibit 97% identity; 2. The size and distribution of the mRNAs are different in the two species; in particular, mRNA was not detected in the dog brain, but is readily observed in the mouse brain; 3. There is a low degree of homology, ≈44%, at the 3' untranslated region of the transporters. Concerning the human gene, a similar argument can be made. Specifically, the deduced amino acid sequence of hS1a displays about 91% identity with the dog transporter, and 88% with the mouse. Further, the human gene was cloned from a brain cDNA library, indicating that the mRNA is present in human brain. Last, the 3' untranslated region of hBGT displays only ≈60% identity with the dog and ≈43% identity with the mouse.

Alternatively, the human gene may in fact be the species homologue of the dog and mouse gene. Although 88–91% amino acid identity is somewhat lower than that observed for species variants of GAT-1, it is similar to the degree of identity between rat and dog versions of the taurine transporter, 90% (Smith et al., 1992; Uchida et al., 1992). Further, the differential distribution may reflect different roles assumed by the same gene product in different species. For example, in the dog BGT might function solely as an osmoregulator in the kidney, via its ability to transport betaine. In the human and mouse it might have assumed the additional role(s) of transporting betaine, and possibly GABA, in the brain. Since the dog transporter is capable of utilizing both betaine and GABA as substrates, the added functions in the mouse and human brain would not require extensive structural changes in the transporter. Last, while the 3' untranslated region is conserved in some species homologues, it is not conserved in others. Regardless of their evolutionary relationship, the cloning of hS1a from a brain cDNA library suggests strongly that hBGT plays a role in brain function in humans.

The ability of BGT to utilize both GABA and betaine as substrates (Yamauchi et al., 1992) leads to interesting questions concerning the physiological role of this transporter. Yamauchi and coworkers noted that the plasma levels of betaine (180 μM) are considerably higher than those of GABA (1 μM) (Yamauchi et al., 1992, and references therein). Thus, despite the 4-fold higher affinity of the transporter for GABA than for betaine, they concluded that in the renal medulla betaine is the physiological substrate. Within the central nervous system, hGBT may transport both GABA and betaine, thereby subserving multiple functions. Because the brain is suspended in a rigid container (ie., the skull), the movement of water must be carefully regulated. Betaine has been detected in brain, where it is thought to serve an osmoregulatory function (Heilig et al., 1989). It is of interest that hBGT displays a high degree of sequence identity (61%) with the transporter for taurine (Smith et al., 1992b), a major osmoregulator in the central nervous system.

As described previously (Borden et al., 1992 and references therein), GABA is the major inhibitory neurotransmitter in the mammalian brain. Termination of GABAergic transmission occurs via transporter-mediated removal of GABA from the synapse. Although the affinity of hBGT for GABA is lower than that of other GABA transporters, its $K_M$ is similar to the concentrations of GABA thought to occur in the synapse (see Mager et al., 1992 for discussion). Thus, BGT may function in the brain to help terminate GABAergic transmission, similar to the role ascribed to other GABA transporters.

Alterations in osmoregulation and in GABAergic transmission have been implicated in a variety of neuropathological and psychiatric conditions. Our cloning of a human betaine/GABA transporter will help elucidate its role in the central nervous system, and will further our understanding of the roles of GABA and betaine in neural function. Additionally, the cloned transporter will aid in the development of specific, high-affinity ligands for this transporter. The use of human gene products in the process of drug development offers significant advantages over those of other species, which may not exhibit the same pharmacologic profiles. The development of such drugs may be useful in a variety of conditions, including (though not restricted to) epilepsy, migraine, ischemia, myoclonus, spasticity, and the treatment of chronic pain.

REFERENCES

Adham, N., Romanienko, P., Hartig, P., Weinshank, R. L., and Branchek, T. 91992) Molec. Pharmacol. 41:1–7.

Amara, S. G. (1992) Nature 360:420–421.

Blakely, R. D., Berson, H. E., Fremeau, Jr., R. T., Caron, M. G., Peek, M. M., Prince, H. K., and Bradley, C. C. (1991) Nature 354:66–70.

Borden, L. A., Smith, K. E., Hartig, P. R., Branchek, T. A., and Weinshank, R. L. (1992) J. Biol. Chem. 267(29):21098–21104.

Christensen, H. N. (1984) Biochim. Biophys. Acta 779:255–269.

Capecchi, M. R., (1989) Science 244: 1288–1292.

Clark, J. A., Deutch, A. Y., Gallipoli, P. Z., and Amara, S. G. (1992) Neuron 9:337–348.

Cohen, J. S., (1989) Trends in Pharm. Sci. 10:435.

Fremeau, Jr., R. T., Caron, M. G., and Blakely, R. D. 1992) Neuron 8:915–926.

Giros, B., El Mestikawy, S., Godinot, N., Zheng, K., Han, H., Yang-Fen, T., and Caron, M. G. (1992) Molec. Pharmacol. 42:383–390.

Guastella, J., Nelson, N., Nelson, H., Czyzyk, L., Keynan, S., Miedel, M. C., Davidson, N., Lester, H. A., and Kanner, B. I. (1990) Science 249:1303-13-6.

Guastella, J., Brecha, N., Weigmann, C., and Lester, H. A. (1992) Proc. Natl. Acad. Sci. 89:7189–7193.

Heilig, C. W., Stromski, M. E., Blumenfeld, J. D., Lee, J. P., and Gullans, S. R. (1989) Am J. Physiol. 257:1108–1116.

Hoffman, B. J., Mezey, E., and Brownstein, M. J. (1991) Science 254:579–580.

Hogan, B., et al., (1986) Manipulating the Mouse Embryo, A Laboratory Manual, Cold Spring Laboratory.

Kanai, Y. and Hediger, M. A. (1992) Nature 360:467–471.

Kanner, B. I. and Schuldiner, S. (1987) in CRC Critical Reviews in Biochemistry 22(1); 1–38.

Kilty, J. E., Lorang, D., and Amara, S. G. (1991) Science 254:578–579.

Liu, Q.-R., Mandiyan, S., Nelson, H., and Nelson, N. (1992a) Proc. Natl. Acad. Sci. 89:6639–6643.

Liu, Q.-R., Nelson, H., Mandiyan, S., Lopez-Corcuera, B., and Nelson, N. (1992b) FEBS 305(2):110–114.

Lopata, M. A., Cleveland, D. W., and Sollner-Webb, B. (1984). Nucl. Acids Res. 12, 5707–5717.

Lopez-Corcuera, B., Liu, Q.-R., Mandiyan, S., Nelson, H., and Nelson, N. (1992) J. Biol. Chem. 267(25):17491–17493.

Low, M. J., R. M. Lechan and R. E. Hammer, (1986) Science 231: 1002–1004.

Mager, S., Quick, M., Labarca, C., Davidson, N., and Lester, H. A. Neuron, in press Maniatis, T., E. F. Fritsch, and J. Sambrook, Molecular Cloning Manual, Cold Spring Harbor Laboratory, Cold Spring Harbor N.Y. (1982).

Miller, J. and Germain, R. N. (1986) J. Exp. Med. 164:1478–1489.

Nelson, H., Mandiyan, S., and Nelson, N. (1990) FEBS 269(1):181–184.

Oberdick, J., Smeyne, R. J., Mann, J. R., Jackson, S. and Morgan, J. I. (1990) Science 248:223–226.

Pacholczyk, T., Blakely, R. D., and Amara, S. G. (1991) Nature 350:350–354.

Pines, G., Danboldt, N. C., Bjoras, M., Zhang, Y., Bendahan, A., Eide, L., Koepsell, H., Storm-Mathisen, J., Seeberg, E., and Kanner, B. I. (1992) Nature 360:464–467.

Sanger, S. (1977) Proc. Natl. Acad. Sci. USA 74:563–5467.

Sarver, N., (1990) Science 247, 1222.

Shimada, S., Kitayama, S., Lin, C.-L., Patel., A., Nanthakumar, E., Gregor, P., Kuhar, M., and Uhl, G. (1991) Science 254:576–578.

Silverman, M. (1991) Annu. Rev. Biochem. 60:757–794.

Smith, K. E., Borden, L. A., Hartig, P. R., Branchek, T., and Weinshank, R. L. (1992a) Neuron 8:927–935.

Smith, K. E., Borden, L. A., Wang, C.-H. D., Hartig, P. R., Branchek, T. A., and Weinshank, R. L. (1992b) Molec. Pharmacol. 42:563–569.

Storck, T., Schulte, S., Hofmann, K., and Stoffel, W. (1992) Proc. Natl. Acad. Sci. 89:10955–10959.

Uchida, S., Kwon, H. M., Yamauchi, A., Preston, A. S., Marumo, F., and Handler, J. S. (1992) Proc. Natl. Acad. Sci. 89:8230–8234.

Uhl, G. R. (1992) Trends in Neurosci. 15(7):265–268.

Uhl, G. R. and Hartig, P. R. (1993) Trends in Pharmacol. Sci., in press.

Usdin, T. B., Mezey, E., Chen, C., Brownstein, M. J., and Hoffman, B. J. (1991) Proc. Natl. Acad. Sci. 88:11168–11171.

Weintraub, H. M., (1990) Scientific American p. January, p. 40.

Yamauchi, A., Uchida, S., Kwon, H. M., Preston, A. S., Robey, R. B., Garcia-Perez, A., Burg, M. B., and Handler, J. S. (1992) J. Biol. Chem. 267(1):649–652.

Zimmer, A. and Gruss, P., (1989) Nature 338, 150–153.

What is claimed is:

1. An isolated nucleic acid molecule encoding a human betaine/GABA transporter having the amino acid sequence shown in FIG. 1 (Seq. I.D. No. 2).

2. A nucleic acid molecule of claim 1, wherein the nucleic acid molecule is a DNA molecule.

3. A DNA molecule of claim 2, wherein the DNA molecule is a cDNA molecule.

4. A DNA molecule of claim 2, wherein the DNA molecule is derived from genomic DNA.

5. A vector comprising a DNA molecule of claim 2.

6. A plasmid vector of claim 5.

7. A vector of claim 5 adapted for expression in a yeast cell which comprises the regulatory elements necessary for the expression of the DNA encoding a betaine\GABA transporter in the yeast cell so located relative to the cDNA as to permit expression thereof.

8. A vector of claim 5 adapted for expression in a mammalian cell which comprises the regulatory elements necessary for expression of the DNA encoding a betaine\GABA transporter in the mammalian cell so located relative to the cDNA as to permit expression thereof.

9. A plasmid of claim 6 adapted for expression in a mammalian cell which comprises the regulatory elements necessary for expression of the DNA in the mammalian cell so located relative to the DNA encoding a betaine\GABA transporter to permit expression thereof.

10. A plasmid of claim 9 designated pcEXV-hBGT (ATCC. Accession No. 75393).

11. A mammalian cell comprising the plasmid of claim 6.

12. A mammalian cell of claim 11, wherein the mammalian cell is an LM (tk−) cell.

13. A mammalain cell of claim 11, wherein the mammalian cell is a COS7 cell.

14. An LM (tk−) cell comprising the plasmid of claim 10 designated L-BGT (ATCC Accession No. CRL11229).

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 2217 base pairs
        ( B ) TYPE: nucleic acid
        ( C ) STRANDEDNESS: double
        ( D ) TOPOLOGY: unknown ( i i ) MOLECULE TYPE: cDNA ( i i i ) HYPOTHETICAL: N ( i v ) ANTI-SENSE: N ( v i i ) IMMEDIATE SOURCE:
        ( A ) LIBRARY: human striatum
        ( B ) CLONE: hS1a ( i x ) FEATURE:
        ( A ) NAME/KEY: CDS
        ( B ) LOCATION: 211..2052
        ( D ) OTHER INFORMATION:

( x i ) SEQUENCE DESCRIPTION: SEQ ID NO:1:

```
TTGGGACTCT CCTGGAGACC TGATGCCCAC AGCCAAGCTG ACCACAGGAG CCGGTGCTGG        60

GGACTGAGGG AAACTTAGAG TTCAGAGAGG GGGTGTGATT TGCCTGAGGT CACACAGCAA       120

GTTAGAGACC CAGCTCCACG ACTCATTGTC TTGGCTTTGG CCCTCGTCAT CCTGCCCACC       180

CAGCGGGGCT TCCCAACCCA CCACACAGCC ATG GAC GGG AAG GTG GCA GTG CAA       234
                                  Met Asp Gly Lys Val Ala Val Gln
                                   1               5

GAG TAT GGG CCT CCT GCA GTC TCC TGG GTC CCC GAG GAG GGA GAG AAG        282
Glu Tyr Gly Pro Pro Ala Val Ser Trp Val Pro Glu Glu Gly Glu Lys
         10                  15                  20

TTG GAC CAG GAA GAC GAG GAC CAG GTG AAG GAT CGG GGC CAA TGG ACC        330
Leu Asp Gln Glu Asp Glu Asp Gln Val Lys Asp Arg Gly Gln Trp Thr
 25                  30                  35                  40

AAC AAG ATG GAG TTT GTG CTG TCA GTG GCC GGG GAG ATC ATT GGG CTG        378
Asn Lys Met Glu Phe Val Leu Ser Val Ala Gly Glu Ile Ile Gly Leu
                 45                  50                  55

GGC AAT GTC TGG AGG TTT CCC TAT CTC TGC TAC AAA AAC GGA GGT GGA        426
Gly Asn Val Trp Arg Phe Pro Tyr Leu Cys Tyr Lys Asn Gly Gly Gly
             60                  65                  70

GCC TTC TTC ATC CCC TAC TTC ATC TTC TTC TTT GTC TGC GGC ATC CCG        474
Ala Phe Phe Ile Pro Tyr Phe Ile Phe Phe Phe Val Cys Gly Ile Pro
         75                  80                  85

GTG TTC TTC CTG GAG GTG GCG TTG GGC CAA TAC ACC AGC CAA GGG AGT        522
Val Phe Phe Leu Glu Val Ala Leu Gly Gln Tyr Thr Ser Gln Gly Ser
 90                  95                 100

GTC ACA GCC TGG AGG AAG ATC TGC CCC CTC TTC CAG GGC ATT GGT CTG        570
Val Thr Ala Trp Arg Lys Ile Cys Pro Leu Phe Gln Gly Ile Gly Leu
105                 110                 115                 120

GCA TCT GTG GTC ATC GAG TCA TAT TTG AAT GTC TAC TAC ATC ATC ATC        618
Ala Ser Val Val Ile Glu Ser Tyr Leu Asn Val Tyr Tyr Ile Ile Ile
                125                 130                 135

CTT GCC TGG GCT CTC TTC TAC CTG TTC AGC TCC TTC ACC TCT GAG CTG        666
Leu Ala Trp Ala Leu Phe Tyr Leu Phe Ser Ser Phe Thr Ser Glu Leu
            140                 145                 150

CCC TGG ACG ACC TGC AAC AAC TTT TGG AAC ACA GAG CAT TGC ACG GAC        714
```

```
              Pro Trp Thr Thr Cys Asn Asn Phe Trp Asn Thr Glu His Cys Thr Asp
                      155                 160                 165
TTT CTG AAC CAC TCA GGA GCC GGC ACA GTG ACC CCA TTT GAG AAT TTT              762
Phe Leu Asn His Ser Gly Ala Gly Thr Val Thr Pro Phe Glu Asn Phe
        170                 175                 180

ACC TCA CCT GTC ATG GAA TTC TGG GAG AGA CGA GTT CTG GGC ATC ACC              810
Thr Ser Pro Val Met Glu Phe Trp Glu Arg Arg Val Leu Gly Ile Thr
185                 190                 195                 200

TCG GGC ATC CAT GAC CTG GGC TCC CTG CGC TGG GAG CTG GCC CTG TGC              858
Ser Gly Ile His Asp Leu Gly Ser Leu Arg Trp Glu Leu Ala Leu Cys
                        205                 210                 215

CTC CTG CTC GCC TGG GTC ATC TGC TAT TTC TGC ATC TGG AAG GGG GTC              906
Leu Leu Leu Ala Trp Val Ile Cys Tyr Phe Cys Ile Trp Lys Gly Val
                220                 225                 230

AAG TCC ACA GGC AAG GTG GTT TAT TTC ACA GCC ACG TTT CCG TAC CTG              954
Lys Ser Thr Gly Lys Val Val Tyr Phe Thr Ala Thr Phe Pro Tyr Leu
        235                 240                 245

ATG CTT GTC ATT TTG CTG ATC AGA GGT GTC ACC CTT CCC GGA GCC TAC             1002
Met Leu Val Ile Leu Leu Ile Arg Gly Val Thr Leu Pro Gly Ala Tyr
250                 255                 260

CAG GGC ATC ATC TAC TAC TTG AAG CCA GAT TTG TTC CGC CTC AAG GAC             1050
Gln Gly Ile Ile Tyr Tyr Leu Lys Pro Asp Leu Phe Arg Leu Lys Asp
265                 270                 275                 280

CCT CAG GTG TGG ATG GAT GCG GGC ACC CAG ATC TTC TTC TCC TTT GCC             1098
Pro Gln Val Trp Met Asp Ala Gly Thr Gln Ile Phe Phe Ser Phe Ala
                        285                 290                 295

ATC TGC CAG GGG TGC CTG ACA GCC CTG GGC AGC TAC AAC AAG TAT CAC             1146
Ile Cys Gln Gly Cys Leu Thr Ala Leu Gly Ser Tyr Asn Lys Tyr His
                300                 305                 310

AAC AAC TGC TAC AAG GAC TGC ATC GCC CTC TGC TTC CTG AAC AGT GCC             1194
Asn Asn Cys Tyr Lys Asp Cys Ile Ala Leu Cys Phe Leu Asn Ser Ala
        315                 320                 325

ACC AGC TTT GTG GCT GGG TTT GTT GTC TTC TCC ATC CTG GGC TTC ATG             1242
Thr Ser Phe Val Ala Gly Phe Val Val Phe Ser Ile Leu Gly Phe Met
330                 335                 340

TCC CAA GAG CAA GGG GTG CCC ATT TCT GAA GTG GCC GAG TCA GGT CCT             1290
Ser Gln Glu Gln Gly Val Pro Ile Ser Glu Val Ala Glu Ser Gly Pro
345                 350                 355                 360

GGG CTG GCC TTC ATC GCC TTC CCC AAG GCT GTG ACT ATG ATG CCC TTA             1338
Gly Leu Ala Phe Ile Ala Phe Pro Lys Ala Val Thr Met Met Pro Leu
                        365                 370                 375

TCC CAG CTG TGG TCC TGC CTG TTC TTT ATC ATG CTC ATA TTC CTA GGG             1386
Ser Gln Leu Trp Ser Cys Leu Phe Phe Ile Met Leu Ile Phe Leu Gly
                380                 385                 390

CTG GAC AGC CAG TTT GTC TGT GTG GAG TGC CTG GTG ACA GCC TCC ATA             1434
Leu Asp Ser Gln Phe Val Cys Val Glu Cys Leu Val Thr Ala Ser Ile
        395                 400                 405

GAC ATG TTC CCC AGG CAG CTC CGG AAG AGC GGG CGG CGC GAG CTC CTC             1482
Asp Met Phe Pro Arg Gln Leu Arg Lys Ser Gly Arg Arg Glu Leu Leu
410                 415                 420

ATC CTC ACC ATC GCC GTC ATG TGC TAC CTG ATA GGG CTT TTC CTG GTC             1530
Ile Leu Thr Ile Ala Val Met Cys Tyr Leu Ile Gly Leu Phe Leu Val
425                 430                 435                 440

ACC GAG GGC GGG ATG TAC ATC TTC CAG CTG TTT GAC TAC TAT GCT TCC             1578
Thr Glu Gly Gly Met Tyr Ile Phe Gln Leu Phe Asp Tyr Tyr Ala Ser
                        445                 450                 455

AGT GGC ATA TGC CTG CTG TTC CTG TCA TTG TTT GAA GTG GTC TGC ATA             1626
Ser Gly Ile Cys Leu Leu Phe Leu Ser Leu Phe Glu Val Val Cys Ile
                460                 465                 470

AGC TGG GTG TAT GGG GCG GAC CGT TTC TAT GAC AAC ATT GAG GAC ATG             1674
```

| | | | | | | | | | | | | | | |
|---|---|---|---|---|---|---|---|---|---|---|---|---|---|---|
|Ser|Trp|Val|Tyr|Gly|Ala|Asp|Arg|Phe|Tyr|Asp|Asn|Ile|Glu|Asp|Met|
| |475| | | |480| | | | |485| | | | |

ATT GGC TAC CGG CCA TGG CCC CTG GTG AAG ATC TCC TGG CTC TTC CTG    1722
Ile Gly Tyr Arg Pro Trp Pro Leu Val Lys Ile Ser Trp Leu Phe Leu
    490             495                 500

ACC CCT GGA CTT TGC CTG GCC ACT TTC CTC TTC TCC TTG AGC AAG TAC    1770
Thr Pro Gly Leu Cys Leu Ala Thr Phe Leu Phe Ser Leu Ser Lys Tyr
505                 510                 515                 520

ACC CCC CTC AAG TAC AAC AAC GTC TAT GTG TAC CCG CCC TGG GGA TAC    1818
Thr Pro Leu Lys Tyr Asn Asn Val Tyr Val Tyr Pro Pro Trp Gly Tyr
                525                 530                 535

TCC ATT GGC TGG TTC CTG GCT CTG TCC TCC ATG GTC TGT GTC CCA CTC    1866
Ser Ile Gly Trp Phe Leu Ala Leu Ser Ser Met Val Cys Val Pro Leu
            540                 545                 550

TTC GTC GTC ATC ACC CTC CTG AAG ACT CGG GGT CCT TTC AGG AAG CGT    1914
Phe Val Val Ile Thr Leu Leu Lys Thr Arg Gly Pro Phe Arg Lys Arg
        555                 560                 565

CTG CGT CAG CTC ATC ACC CCT GAC TCC AGT CTG CCA CAG CCC AAG CAA    1962
Leu Arg Gln Leu Ile Thr Pro Asp Ser Ser Leu Pro Gln Pro Lys Gln
    570                 575                 580

CAT CCC TGC TTG GAT GGC AGT GCT GGC CGG AAC TTT GGG CCC TCC CCA    2010
His Pro Cys Leu Asp Gly Ser Ala Gly Arg Asn Phe Gly Pro Ser Pro
585                 590                 595                 600

ACA AGG GAA GGA CTG ATA GCC GGG GAG AAG GAG ACC CAT TTG            2052
Thr Arg Glu Gly Leu Ile Ala Gly Glu Lys Glu Thr His Leu
                605                 610

TAGGGTGTGA CCAGAGGCCA GGCGGCTCCT AAGCCGGGAA CCTAGGTCAG GGCCACCCTC    2112

CATTCTCAGC GGACAGCCTC TGCCTCTGTC TCCTGCCACA ATCCTGCTGG GAACCTCTGG    2172

AGAGCCACAG GCACCCCCAG CTGGAGGCCA GACTCCTCTC TTGTG                  2217

( 2 ) INFORMATION FOR SEQ ID NO:2:

( i ) SEQUENCE CHARACTERISTICS:
        ( A ) LENGTH: 614 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

Met Asp Gly Lys Val Ala Val Gln Glu Tyr Gly Pro Pro Ala Val Ser
1               5                   10                  15

Trp Val Pro Glu Glu Gly Glu Lys Leu Asp Gln Glu Asp Glu Asp Gln
            20                  25                  30

Val Lys Asp Arg Gly Gln Trp Thr Asn Lys Met Glu Phe Val Leu Ser
        35                  40                  45

Val Ala Gly Glu Ile Ile Gly Leu Gly Asn Val Trp Arg Phe Pro Tyr
    50                  55                  60

Leu Cys Tyr Lys Asn Gly Gly Ala Phe Phe Ile Pro Tyr Phe Ile
65                  70                  75                  80

Phe Phe Phe Val Cys Gly Ile Pro Val Phe Phe Leu Glu Val Ala Leu
                85                  90                  95

Gly Gln Tyr Thr Ser Gln Gly Ser Val Thr Ala Trp Arg Lys Ile Cys
            100                 105                 110

Pro Leu Phe Gln Gly Ile Gly Leu Ala Ser Val Val Ile Glu Ser Tyr
        115                 120                 125

Leu Asn Val Tyr Tyr Ile Ile Ile Leu Ala Trp Ala Leu Phe Tyr Leu
    130                 135                 140

-continued

| | | | | | | | | | | | | | | | |
|---|---|---|---|---|---|---|---|---|---|---|---|---|---|---|---|
| Phe | Ser | Ser | Phe | Thr | Ser | Glu | Leu | Pro | Trp | Thr | Thr | Cys | Asn | Asn | Phe |
| 145 | | | | 150 | | | | | 155 | | | | | | 160 |
| Trp | Asn | Thr | Glu | His | Cys | Thr | Asp | Phe | Leu | Asn | His | Ser | Gly | Ala | Gly |
| | | | 165 | | | | | 170 | | | | | 175 | | |
| Thr | Val | Thr | Pro | Phe | Glu | Asn | Phe | Thr | Ser | Pro | Val | Met | Glu | Phe | Trp |
| | | | 180 | | | | | 185 | | | | | 190 | | |
| Glu | Arg | Arg | Val | Leu | Gly | Ile | Thr | Ser | Gly | Ile | His | Asp | Leu | Gly | Ser |
| | | 195 | | | | | 200 | | | | | 205 | | | |
| Leu | Arg | Trp | Glu | Leu | Ala | Leu | Cys | Leu | Leu | Ala | Trp | Val | Ile | Cys | |
| | 210 | | | | | 215 | | | | 220 | | | | | |
| Tyr | Phe | Cys | Ile | Trp | Lys | Gly | Val | Lys | Ser | Thr | Gly | Lys | Val | Val | Tyr |
| 225 | | | | | 230 | | | | | 235 | | | | | 240 |
| Phe | Thr | Ala | Thr | Phe | Pro | Tyr | Leu | Met | Leu | Val | Ile | Leu | Leu | Ile | Arg |
| | | | | 245 | | | | | 250 | | | | | 255 | |
| Gly | Val | Thr | Leu | Pro | Gly | Ala | Tyr | Gln | Gly | Ile | Ile | Tyr | Tyr | Leu | Lys |
| | | | 260 | | | | | 265 | | | | | 270 | | |
| Pro | Asp | Leu | Phe | Arg | Leu | Lys | Asp | Pro | Gln | Val | Trp | Met | Asp | Ala | Gly |
| | | 275 | | | | | 280 | | | | | 285 | | | |
| Thr | Gln | Ile | Phe | Phe | Ser | Phe | Ala | Ile | Cys | Gln | Gly | Cys | Leu | Thr | Ala |
| | 290 | | | | | 295 | | | | 300 | | | | | |
| Leu | Gly | Ser | Tyr | Asn | Lys | Tyr | His | Asn | Asn | Cys | Tyr | Lys | Asp | Cys | Ile |
| 305 | | | | | 310 | | | | | 315 | | | | | 320 |
| Ala | Leu | Cys | Phe | Leu | Asn | Ser | Ala | Thr | Ser | Phe | Val | Ala | Gly | Phe | Val |
| | | | | 325 | | | | | 330 | | | | | 335 | |
| Val | Phe | Ser | Ile | Leu | Gly | Phe | Met | Ser | Gln | Glu | Gln | Gly | Val | Pro | Ile |
| | | | 340 | | | | | 345 | | | | | 350 | | |
| Ser | Glu | Val | Ala | Glu | Ser | Gly | Pro | Gly | Leu | Ala | Phe | Ile | Ala | Phe | Pro |
| | | | 355 | | | | | 360 | | | | | 365 | | |
| Lys | Ala | Val | Thr | Met | Met | Pro | Leu | Ser | Gln | Leu | Trp | Ser | Cys | Leu | Phe |
| | 370 | | | | | 375 | | | | | 380 | | | | |
| Phe | Ile | Met | Leu | Ile | Phe | Leu | Gly | Leu | Asp | Ser | Gln | Phe | Val | Cys | Val |
| 385 | | | | | 390 | | | | | 395 | | | | | 400 |
| Glu | Cys | Leu | Val | Thr | Ala | Ser | Ile | Asp | Met | Phe | Pro | Arg | Gln | Leu | Arg |
| | | | | 405 | | | | | 410 | | | | | 415 | |
| Lys | Ser | Gly | Arg | Arg | Glu | Leu | Leu | Ile | Leu | Thr | Ile | Ala | Val | Met | Cys |
| | | | 420 | | | | | 425 | | | | | 430 | | |
| Tyr | Leu | Ile | Gly | Leu | Phe | Leu | Val | Thr | Glu | Gly | Gly | Met | Tyr | Ile | Phe |
| | | 435 | | | | | 440 | | | | | 445 | | | |
| Gln | Leu | Phe | Asp | Tyr | Tyr | Ala | Ser | Ser | Gly | Ile | Cys | Leu | Leu | Phe | Leu |
| | 450 | | | | | 455 | | | | | 460 | | | | |
| Ser | Leu | Phe | Glu | Val | Val | Cys | Ile | Ser | Trp | Val | Tyr | Gly | Ala | Asp | Arg |
| 465 | | | | | 470 | | | | | 475 | | | | | 480 |
| Phe | Tyr | Asp | Asn | Ile | Glu | Asp | Met | Ile | Gly | Tyr | Arg | Pro | Trp | Pro | Leu |
| | | | | 485 | | | | | 490 | | | | | 495 | |
| Val | Lys | Ile | Ser | Trp | Leu | Phe | Leu | Thr | Pro | Gly | Leu | Cys | Leu | Ala | Thr |
| | | | 500 | | | | | 505 | | | | | 510 | | |
| Phe | Leu | Phe | Ser | Leu | Ser | Lys | Tyr | Thr | Pro | Leu | Lys | Tyr | Asn | Asn | Val |
| | | 515 | | | | | 520 | | | | | 525 | | | |
| Tyr | Val | Tyr | Pro | Pro | Trp | Gly | Tyr | Ser | Ile | Gly | Trp | Phe | Leu | Ala | Leu |
| | 530 | | | | | 535 | | | | | 540 | | | | |
| Ser | Ser | Met | Val | Cys | Val | Pro | Leu | Phe | Val | Val | Ile | Thr | Leu | Leu | Lys |
| 545 | | | | | 550 | | | | | 555 | | | | | 560 |
| Thr | Arg | Gly | Pro | Phe | Arg | Lys | Arg | Leu | Arg | Gln | Leu | Ile | Thr | Pro | Asp |
| | | | | 565 | | | | | 570 | | | | | 575 | |

```
Ser  Ser  Leu  Pro  Gln  Pro  Lys  Gln  His  Pro  Cys  Leu  Asp  Gly  Ser  Ala
               580                      585                     590

Gly  Arg  Asn  Phe  Gly  Pro  Ser  Pro  Thr  Arg  Glu  Gly  Leu  Ile  Ala  Gly
               595                      600                     605

Glu  Lys  Glu  Thr  His  Leu
     610
```